(12) United States Patent
Kountotsis

(10) Patent No.: US 8,872,656 B2
(45) Date of Patent: *Oct. 28, 2014

(54) SYSTEM AND METHOD FOR PERFORMING CHEMICAL ANALYSIS OF FINGERPRINTS FOR PROVIDING AT LEAST ONE RESPONSE

(71) Applicant: Theodosios Kountotsis, Melville, NY (US)

(72) Inventor: Theodosios Kountotsis, Melville, NY (US)

(*) Notice: Subject to any disclaimer, the term of this patent is extended or adjusted under 35 U.S.C. 154(b) by 45 days.

This patent is subject to a terminal disclaimer.

(21) Appl. No.: 13/858,369

(22) Filed: Apr. 8, 2013

(65) Prior Publication Data

US 2013/0276535 A1 Oct. 24, 2013

Related U.S. Application Data

(63) Continuation of application No. 12/927,511, filed on Nov. 17, 2010, now Pat. No. 8,461,987.

(51) Int. Cl.
  *G08B 21/00* (2006.01)
  *A61B 5/117* (2006.01)
  *G01N 33/00* (2006.01)
  *G01N 33/50* (2006.01)
  *G06K 9/00* (2006.01)
  *G06F 3/0354* (2013.01)
  *A61B 5/145* (2006.01)
  *G07C 9/00* (2006.01)

(52) U.S. Cl.
  CPC .............. *A61B 5/1172* (2013.01); *G01N 33/00* (2013.01); *G01N 33/5005* (2013.01); *G06K 9/00006* (2013.01); *G06F 3/03547* (2013.01); *G06K 9/00892* (2013.01); *A61B 5/14517* (2013.01); *G06F 2203/0338* (2013.01); *G07C 9/00158* (2013.01)
  USPC ........................... 340/540; 340/908; 340/5.83

(58) Field of Classification Search
  USPC .............. 340/540, 5.83, 908, 5.82, 5.8, 5.86, 340/5.91, 7.55, 546, 586
  See application file for complete search history.

(56) References Cited

U.S. PATENT DOCUMENTS

| | | | |
|---|---|---|---|
| 8,461,987 B2 * | 6/2013 | Kountotsis | 340/540 |
| 2007/0077595 A1 * | 4/2007 | Koo et al. | 435/7.1 |
| 2008/0167197 A1 * | 7/2008 | Schmidt et al. | 506/6 |
| 2010/0028945 A1 * | 2/2010 | Klaenhammer et al. | 435/69.1 |

* cited by examiner

*Primary Examiner* — Daniel Previl
(74) *Attorney, Agent, or Firm* — Theodosios Kountotsis

(57) ABSTRACT

An electronic device is presented including a fingerprint collecting module for collecting fingerprint information and a chemical analysis module for performing a chemical analysis of the fingerprint information to create a chemical profile for identifying at least a select number of molecules and/or organic compounds for deriving distinguishing characteristics from the fingerprint information. The electronic device may also include an evaluating module for evaluating the distinguishing characteristics of the fingerprint information to provide at least one response formulated from the distinguishing characteristics derived from the select number of molecules and/or organic compounds.

20 Claims, 13 Drawing Sheets

SYSTEM AND METHOD FOR PERFORMING CHEMICAL ANALYSIS OF FINGERPRINTS FOR PROVIDING AT LEAST ONE RESPONSE

CROSS-REFERENCE TO RELATED APPLICATIONS

This application is a continuation of U.S. patent application Ser. No. 12/927,511, filed on Nov. 17, 2010, the entire disclosure of which is incorporated by reference herein.

BACKGROUND

1. Field of the Related Art

The present disclosure relates to fingerprint recognition technology, and more particularly, but not exclusively, to methods and systems for performing a chemical analysis of fingerprints for providing, in certain instances, at least one substantially instant response, such as a reply, result, recommendation, supplemental information and/or feedback.

2. Description of the Related Art

The need to identify and authenticate individuals is greater today than it has ever been, and is particularly acute for applications such as homeland security, law enforcement, electronic commerce, access control and privacy protection, to name a few.

The use of biometrics in general, and fingerprint recognition in particular, to identify and authenticate humans is a proven method. Biometrics is a group of technologies that provide a high level of security. Fingerprint capture and recognition is an important biometric technology. Law enforcement, banking, voting, retail, and other industries increasingly rely upon fingerprints as a biometric to recognize or verify identity.

Fingerprint identification systems usually involve the use of a computer, which provides an identification probability for a match of a fingerprint to a prerecorded fingerprint held in a database. In this manner, fingerprint recognition devices have been employed for accessing high security areas. Fingerprint scanners are one form of fingerprint recognition devices. Fingerprint scanners having image sensors are available, which capture an image of a fingerprint. A signal representative of the captured image is then sent over a data communication interface to a host computer for further processing.

However, to perform identification and authentication in many of the applications envisaged today, quick and accurate collection of several samples of fingerprints in various environments is important. Thus, there is a need for automated fingerprint recognition, where a large number of fingerprints may be collected and analyzed from various environments or electronic devices without sacrificing accuracy. Thus, there is a need in the fingerprint recognition art for a technological solution that overcomes at least in part the aforesaid deficiencies.

SUMMARY

The present disclosure provides a fingerprint recognition system including a fingerprint collecting module positioned about an electronic device for collecting fingerprint information related to one or more fingerprints; a chemical analysis module for performing a chemical analysis of the fingerprint information collected; and an evaluating module for evaluating the chemical analysis of the fingerprint information collected to provide at least one response.

The present disclosure also provides a method of recognizing and evaluating one or more fingerprints, including receiving the one or more fingerprints from a fingerprint collecting module positioned about an electronic device; performing a chemical analysis of the one or more fingerprints; and providing at least one response based on the chemical analysis of the one or more fingerprints.

The present disclosure also provides a chemical analysis system for performing substantially instantaneous chemical analysis of received fingerprints and providing substantially instantaneous recommendations or feedback or responses based on the chemical analysis of the fingerprints received.

The present disclosure also provides a fingerprint analysis system, including a processor; a computer-readable storage medium in communication with the processor, the computer-readable storage medium comprising one or more programming instructions for: receiving the one or more fingerprints from a fingerprint collecting module positioned about an electronic device; performing a chemical analysis of the one or more fingerprints; and providing at least one response based on the chemical analysis of the fingerprints.

The present disclosure also provides a fingerprint analysis system, including a processor; a computer-readable storage medium in communication with the processor, the computer-readable storage medium comprising one or more programming instructions for: providing a chemical analysis system for performing substantially instantaneous chemical analysis of received fingerprints and providing substantially instantaneous recommendations or feedback or responses based on the chemical analysis of the fingerprints received.

The present disclosure also provides a method of matching individuals. The method includes the steps of: inputting a first fingerprint via a first electronic device; performing a chemical analysis of the first fingerprint; determining attributes and/or characteristics of the first fingerprint; inputting a second fingerprint via a second electronic device, performing a chemical analysis of the second fingerprint; determining attributes and/or characteristics of the second fingerprint; bringing the first electronic device in close proximity to the second electronic device; allowing communication between the first electronic device and the second electronic device; comparing a first personality profile with a second personality profile; determining a match; and transmitting a personality match probability to the first and second electronic devices.

The present disclosure further provides a method of matching individuals via personality profiles. The method includes the steps of: providing a plurality of electronic devices having chemical analysis capabilities of fingerprints; obtaining one or more chemical analysis samples from a plurality of individuals who operate or own the plurality of electronic devices; deriving a plurality of attributes or characteristics of the plurality of individuals; recording the plurality of attributes or characteristics of the plurality of individuals, either in a local or remote storage module (or database); and using the plurality of electronic devices to determine or detect or predict a compatibility match between the plurality of individuals based on correlations between one or more generic or specific attributes and/or characteristics.

Further scope of applicability of the present disclosure will become apparent from the detailed description given hereinafter. However, it should be understood that the detailed description and specific examples, while indicating preferred embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

Various embodiments of the present disclosure will be described herein below with reference to the figures wherein.

Figure 1:
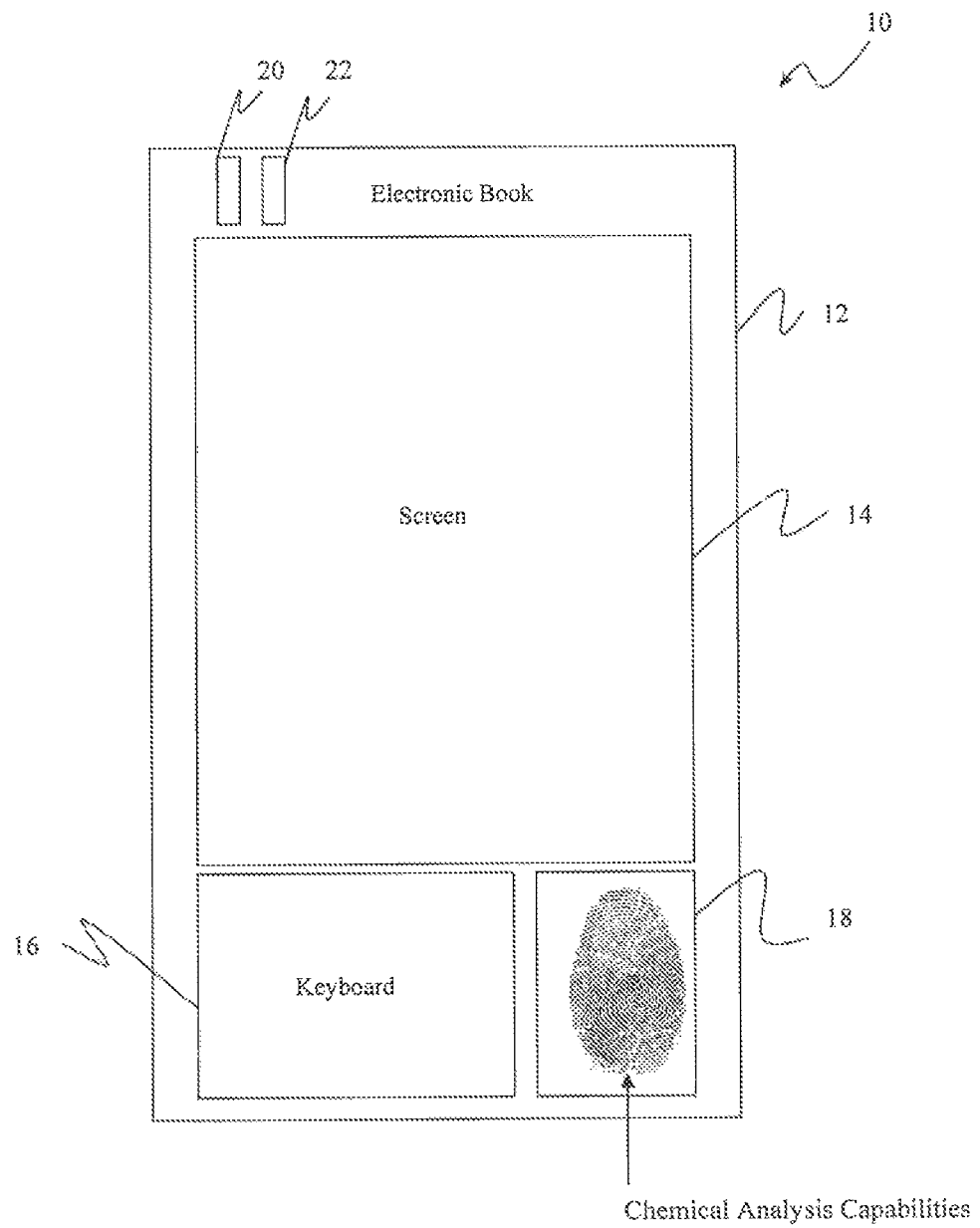
FIG. 1 is an electronic book including a fingerprint input, recognition, and collection device having chemical analysis capabilities, in accordance with the present disclosure.

It is noted that the drawings of the present disclosure are not to scale. The drawings are intended to depict only typical embodiments of the present disclosure, and therefore should not be considered as limiting the scope of the present disclosure. In the drawings, like numbering represents like elements between the drawings.

DETAILED DESCRIPTION

Although the present disclosure will be described in terms of a specific embodiment, it will be readily apparent to those skilled in this art that various modifications, rearrangements and substitutions may be made without departing from the spirit of the present disclosure. The scope of the present disclosure is defined by the claims appended hereto.

For the purposes of promoting an understanding of the principles of the present disclosure, reference will now be made to the exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

Reference throughout this specification to "one embodiment," "an embodiment," or similar language means that a particular feature, structure, or characteristic described in connection with the embodiment is included in at least one embodiment of the present disclosure. Thus, appearances of the phrases "one embodiment," "an embodiment," and similar language throughout this specification may, but do not necessarily, all refer to the same embodiment, different embodiments, or component parts of the same or different illustrated disclosure. Additionally, reference to the wording "an embodiment," or the like, for two or more features, elements, etc. does not mean that the features are related, dissimilar, the same, etc. The use of the term "an embodiment," or similar wording, is merely a convenient phrase to indicate optional features, which may or may not be part of the present disclosure as claimed. The independent embodiments are considered to be able to be combined in whole or in part one with another as the claims and/or art may direct, either directly or indirectly, implicitly or explicitly.

Moreover, the fact that the wording "an embodiment," or the like, does not appear at the beginning of every sentence in the specification, such as is the practice of some practitioners, is merely a convenience for the reader's clarity. However, it is the intention of this application to incorporate by reference the phrasing "an embodiment," and the like, at the beginning of every sentence herein where logically possible and appropriate.

Prior to describing the present disclosure in further detail, it will first be helpful to define various terms that will be used throughout the following discussion. For example:

In this application, the use of the singular includes the plural unless specifically stated otherwise. In this application, the use of "or" means "and/or" unless stated otherwise. Furthermore, the use of the term "including," as well as other forms, such as "includes" and "included," is not limiting. Also, terms such as "element" or "component" encompass both elements and components comprising one unit and elements and components that comprise more than one subunit unless specifically stated otherwise.

The term "analyze" or "analysis" may at least refer to determining the elements or essential features or functions or processes of one or more fingerprint recognition, collection, and analysis systems for computational processing. The term "analyze" may further refer to tracking data and/or collecting data and/or manipulating data and/or examining data and/or updating data on a real-time basis in an automatic manner and/or a selective manner and/or manual manner (continuously or periodically or intermittently).

The term "module" or "unit" may at least refer to a self-contained component (unit or item) that may be used in combination with other components and/or a separate and distinct unit of hardware or software that may be used as a component in a system, such as a fingerprint system. The term "module" may at least refer to a self-contained assembly of electronic components and circuitry, such as a stage in a computer that may be installed as a unit. The term "module" may be used interchangeably with the term "unit."

The term "storage" may at least refer to data storage. "Data storage" may refer to any article or material (e.g., a hard disk) from which information may be capable of being reproduced, with or without the aid of any other article or device. "Data storage" may refer to the holding of data in an electromagnetic form for access by a computer processor. Primary storage may be data in random access memory (RAM) and other "built-in" devices. Secondary storage may be data on hard disk, tapes, and other external devices. "Data storage" may also refer to the permanent holding place for digital data, until purposely erased. "Storage" implies a repository that retains its content without power. "Storage" mostly means magnetic disks, magnetic tapes and optical discs (CD, DVD, etc.). "Storage" may also refer to non-volatile memory chips such as flash, Read-Only memory (ROM) and/or Electrically Erasable Programmable Read-Only Memory (EEPROM).

The term "electronic device" may refer at least to one or more personal computers (PCs), a standalone printer, a standalone scanner, a mobile phone, an MP3 player, audio electronics, video electronics, GPS systems, televisions, recording and/or reproducing media (such as CDs, DVDs, camcorders, cameras, etc.) or any other type of consumer or non-consumer analog and/or digital electronics. Such consumer and/or non-consumer electronics may apply at least in any type of entertainment, communications, home, and/or office capacity. Thus, the term "electronic device" may refer to any type of electronics suitable for use with a circuit board and intended to be used by a plurality of individuals for a variety of purposes. The electronic device may be any type of computing and/or processing device.

Additionally, "electronic devices" may refer to at least, or may include but are not limited to, a mouse, keyboard, Bluetooth™ adapter, global positioning system (GPS) receiver, remote control, audio module, user interface module, electronic-book reader module, radio frequency identification (RFID) reader, barcode reader, digital projector, universal serial bus stick, magnetometer, fingerprint reader, current/voltage measuring device, electrocardiogram, pulse measuring device, and stethoscope. Additionally, "electronic devices" may refer to at least, or may include but are not limited to, an electronic book, displays, television sets, electronic paper, watches, electronic calculators, cellular phones, personal digital assistants, cellular telephone, view finder, direct view type video tape recorder, car navigation system, pager, electronic notebook or personal computer (PC), electric calculator, word processor, work station, picture telephone, point of sale (POS) terminal(s), point-of-entry (POE) terminal(s) and any type of electrical or mechanical or electromechanical apparatus/system/configuration with one or more touch panels.

The term "processing" or "processor" may at least refer to determining the elements or essential features or functions or processes of one or more fingerprint recognition, collection, and analysis systems for computational processing. The term "process" or "processor" may further refer to or encompass or include tracking data and/or collecting data and/or manipulating data and/or examining data and/or updating data on a real-time basis in an automatic manner and/or a selective manner and/or manual manner (continuously or periodically or intermittently).

As used herein, the term "fingerprint" or "fingerprint image" may be used to refer to at least any type of detected fingerprint including but not limited to an image of all or part of one or more fingerprints (partial patterns), a rolled fingerprint, a flat stationary fingerprint, a palm print, and/or prints of multiple fingers.

Within this disclosure, the term "user" may also include, in addition to human users: computers, automated systems, controllers, robotic devices, and other electromechanical devices, systems, configurations/apparatuses using software (or code).

In one exemplary embodiment, the present disclosure proposes an electronic device capable of receiving one or more fingerprints, analyzing the chemical features or characteristics or attributes of the one or more fingerprints, and providing one or more responses (e.g., recommendations, results, feedback) to the subject or user of the electronic device.

In the exemplary embodiments, the fingerprint recognition system may be employed for the electrical and optical detection of a plurality of molecules and/or biomolecules and/or organic compounds or any other type of chemical characteristics. In other words, the fingerprint assemblies and/or systems and/or configurations of the exemplary embodiments enable a chemical analysis of a person's fingerprint, preferably, on-the-spot, in real-time, and/or substantially instantaneously or in a short predetermined period of time, such that instant responses are provided to the operator of the electronic device.

In the exemplary embodiments, a fingerprint recognition system is provided for conveying audible messages or voice messages or text or images or videos (or a combination thereof) as responses. The responses provided may refer to a myriad of different possible messages or results or recommendations or feedback for providing additional information or supplemental information or educational information or advertising information to a consumer or user or subject or person.

In the exemplary embodiments, a user of an electronic book (e.g., Amazon® Kindle™ or Nook™ by Barnes and Noble® or Sony® Reader™) may input a fingerprint via a fingerprint system having at least chemical analysis capabilities for analyzing the fingerprint. The fingerprint may be analyzed at least with respect to molecules and/or biomolecules and/or organic compounds. Once the chemical signature or chemical blueprint has been obtained, at least one recommendation may be displayed on the display screen of the electronic book. The recommendation may relate to any topic, including, but not limited to, games, music, social networking, news, weather, sports, maps, navigation search, videos, movies, entertainment, food, drinks, communication, banking, finance, shopping, retail, productivity, travel, and lifestyle or a combination thereof. However, in the instant case, the recommendation may specifically relate to recommendations of other books in a similar category (as the one being read currently on the electronic book) or a different category of books.

Various embodiments are described hereinbelow, including methods and techniques. It should be kept in mind that the present disclosure might also cover articles of manufacture that includes a computer readable medium on which computer-readable instructions for carrying out embodiments of the inventive technique are stored. The computer readable medium may include, for example, semiconductor, magnetic, opto-magnetic, optical, or other forms of computer readable medium for storing computer readable code. Further, the present disclosure may also cover apparatuses for practicing embodiments of the present disclosure. Such apparatus may include circuits, dedicated and/or programmable, to carry out tasks pertaining to embodiments of the present disclosure. Examples of such apparatus include a general-purpose computer and/or a dedicated computing device when appropriately programmed and may include a combination of a computer/computing device and dedicated/programmable circuits adapted for the various tasks pertaining to embodiments of the present disclosure.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Embodiments will be described below while referencing the accompanying figures. The accompanying figures are merely examples and are not intended to limit the scope of the present disclosure.

With reference to FIG. 1, there is presented an electronic book including a fingerprint input, recognition, and collection device having chemical analysis capabilities, in accordance with the present disclosure.

The electronic book 10 includes a housing 12, a display 14, an input device 16, and a fingerprint recognition device 18. Additionally, the electronic book 10 includes an on/off switch 20 and a notification unit 22.

The fingerprint recognition device 18 may be any type of, for example, gelatin sensing mechanism for receiving and analyzing fingerprints. For instance, the gelatin sensing mechanism may be a gel tape for collecting/gathering fingerprints. The fingerprint recognition device 18 may be constructed from one or more biomaterials and/or biochips and/or gel biochips and/or biosensors and/or bio-electronic sensors and/or microprocessors, all of which may or may not be constructed from flexible materials. Biochips, for example, may be employed for the electrical and optical detection of a plurality of molecules and/or biomolecules and/or organic compounds. Of course, the fingerprint recognition device 18 need not be constructed from a gelatin-like material. The fingerprint recognition device 18 may be any type of device for recognizing and collecting fingerprints. Thus, the fingerprint recognition device 18 may support a plurality of scanner and/or sensor types, inclusive of, but not restricted to capacitive, thermal, optical, tactile, or ultrasonic sensors. The application of these sensors is determined by accuracy, user friendliness, and time for processing. The exemplary embodiments of the present disclosure may be implemented by using any of these types of scanners/sensors and/or biomaterials to aid in the substantially instantaneous reception and analysis (e.g., chemical analysis) of one or more fingerprints.

A chemical photograph or signature may be taken instantaneously, on-the-spot, in real-time, while the fingerprint recognition device 18 is positioned on and/or about an electronic device. The chemical photograph or signature or snapshot may automatically, on-the-spot, and in real-time identify at least molecules or organic compounds that differentiate one person from another. For example, males may be detected based on greater amount of urea (one chemical of the urine), since males sweat more urea than women. The chemical photograph or signature or snapshot may include compounds of chemicals that may identify at least the age, gender, race, dietary preferences and/or lifestyle preferences of the subject or person or individual touching/pressing/contacting the fingerprint recognition device 18.

In summary, the electronic device (e.g., electronic book 10) of FIG. 1 is capable of receiving one or more fingerprints, analyzing the chemical features of the one or more fingerprints, and providing one or more responses (e.g., feedback, recommendations, results, etc.) to the subject or user of the electronic device.

The responses are directly based on the inputted fingerprint. For example, if a male touches the fingerprint recognition device 18 and inputs a fingerprint, the responses may be of a first type. For instance, in such exemplary embodiment, the electronic book 10 may display information that may appeal more to a male. Such information may relate to books such a male would prefer (e.g., books related to warfare). Thus, the electronic book 10 may automatically provide a selection of say 10 top books related to warfare. Alternatively, for example, if a female touches the fingerprint recognition device 18 and inputs a fingerprint, the responses may be of a second type. For instance, in such exemplary embodiment, the electronic book 10 may display information that may appeal more to a female (e.g., romance novels). Thus, the electronic book 10 may automatically provide a selection of say 10 top books related to romance. As a result, the audible or voice messages or text or images or videos or information provided as responses are different based on detection of, for example, gender. In other words, the responses or recommendations provided (in a variety of forms) are targeted information (i.e., targeted for a specific audience based on the chemical composition or signature or blueprint received from that person's fingerprint).

Alternatively, one person may touch/press/contact the fingerprint recognition device 18 and the fingerprint recognition device 18 may detect whether that person is a vegetarian or a meat eater. For example, vegetarians may have different amino-acid contents detected than a meat eater. For instance, as a result of such input, the fingerprint recognition device 18 may provide information that may appeals more to a vegetarian, rather than a meat-eater, such as cookbooks for vegetarians. Therefore, the audible messages or voice messages or text or images or videos provided as responses are different based on detection of, for example, a lifestyle characteristic. In other words, the provided responses or recommendations are targeted information (i.e., targeted for a specific audience based on the chemical composition or signature or blueprint received from that person's fingerprint).

Obviously, the audible messages or voice messages or text or images or videos (or a combination thereof) provided as responses may refer to a myriad of different possible messages or results or responses or recommendations or feedback for providing additional information or supplemental information or educational information or advertising information to a consumer or user or subject or person.

Targeted advertising (or targeted information) may be a type of advertising whereby advertisements are placed so as to reach consumers based on various traits such as demographics, age, gender, race, dietary information, smoking behaviors, drinking behaviors and/or lifestyle information or a combination thereof. The advertising (or recommendations or feedback) of the present example embodiments may be targeted interactive and targeted behavioral advertising. The advertising is interactive because a consumer is required to touch/press/contact or physically interact with the fingerprint recognition device 18. The advertising is behavioral because a consumer's preferences are determined to provide recommendations and/or feedback and/or information to the user based on the chemical analysis performed by the fingerprint recognition device 18. In other words, sellers or manufacturers or producers of products/items may wish to convey specific messages to specific types of subjects or people.

In order to accomplish such wish, targeted messages may be incorporated within or transmitted to the electronic book 10 of FIG. 1 having a gel-type adhesive member (e.g., fingerprint recognition device 18) to convey targeted messages based on voluntary user input of a fingerprint. The messages are determined based on probabilities computed by advertisers or marketers or producers or manufacturers or any type of entity that sells, offers, licenses, promotes, etc. such products/items. It is contemplated that any types of electronic device (even a kiosk) may be used with a fingerprint system having chemical analysis capabilities.

The display means 14 may be any type of electronic display, such as a flat panel display device, such as a liquid crystal display ("LCD"), a plasma display panel ("PDP") and an organic light emitting diode ("OLED"). Of course, one skilled in the art may contemplate using any type of display means/device/apparatus/configuration. Such display 14 may be positioned at one or more point-of-sale (POS) or point-of-entry (POE) locations. For example, the user may approach a kiosk (as described below) in a retail store that has the display means 14. The display means 14 may enable the consumer to enter a fingerprint and receive a response based on the chemical composition of the fingerprint (e.g., molecular compounds). The fingerprint may be instantly processed or processed within a predetermined period of time. Once processed, the kiosk may provide the user with audible messages or voice messages or text or images or videos or additional/supplemental information as responses based on detection of, for example, at least age, gender, race, dietary information, lifestyle information etc.). Based on such input, the fingerprint analysis device 18 analyzes the chemical photograph or signature of the fingerprint by identifying and analyzing, for example, the molecules and/or molecular or organic compounds on the fingerprint. Based on the chemical analysis results, the display means 14 may convey audible messages or voice messages or text or images or videos or additional/supplemental information or a combination thereof.

Moreover, the notification unit 22 is used for notifying a subject of one or more updated responses including updated feedback, recommendations, and results, the notification unit 22 being at least one of a sound emitting unit or a visual indication unit.

Of course, these are only non-limiting examples of where such fingerprint recognition device 18 having chemical analysis capabilities may be used. It is contemplated that such fingerprint recognition device 18 having chemical analysis capabilities may be used in any type of industry for any type of application where a user voluntarily inputs a fingerprint and the fingerprint recognition device 18 having chemical analysis capabilities outputs predetermined or updated messages or recommendations instantly, in real-time.

Thus, the chemical analysis of the fingerprint occurs substantially instantaneously with the input or within a short predetermined time period of the input. A match is determined between the chemical composition of the inputted fingerprint and the prerecorded information to determine a probability of which message or messages would be most appropriate based on the inputted fingerprint and subsequent chemical analysis of the fingerprint.

Figure 2:
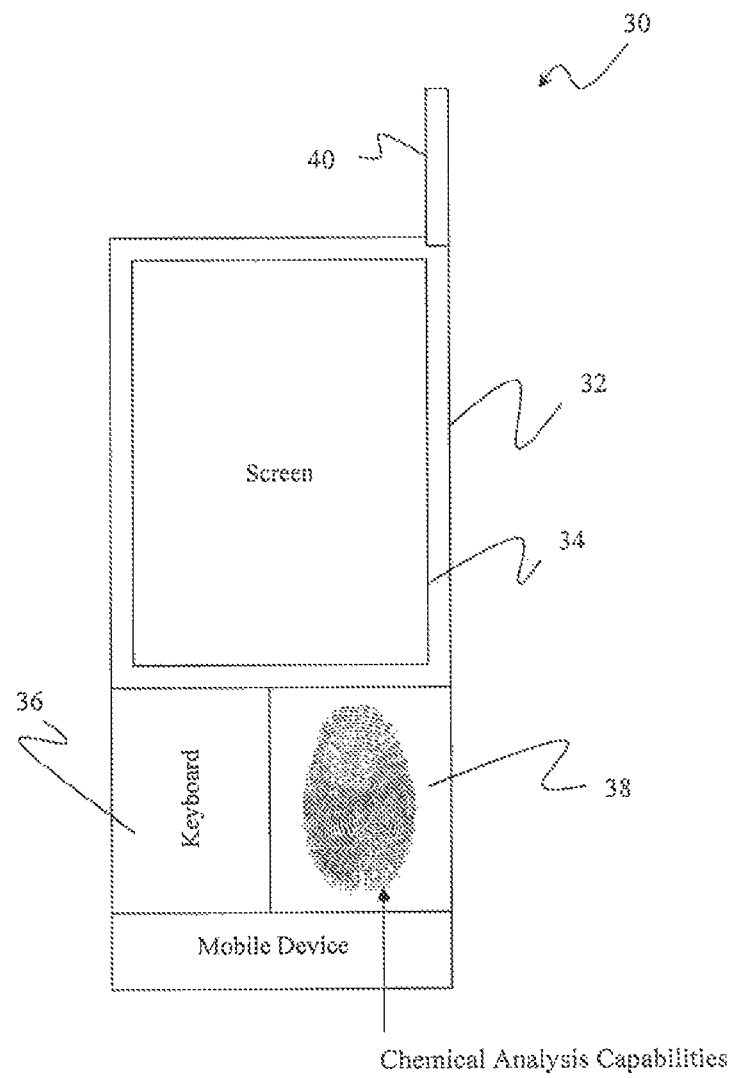
FIG. 2 is a mobile device including a fingerprint input, recognition, and collection device having chemical analysis capabilities, in accordance with the present disclosure.

With reference to FIG. 2, there is presented a mobile device including a fingerprint input, recognition, and collection device having chemical analysis capabilities, in accordance with the present disclosure.

The mobile device 30 includes a housing 32, a display screen 34, an input means 36 (e.g., a keyboard), and a fingerprint recognition system 38 having at least chemical analysis capabilities. The mobile device 30 may also include an antenna 40.

The fingerprint recognition system 38 operates in the same manner as the fingerprint recognition system 18 shown in FIG. 1. In the instant case, cell phone functions and/or cell phone applications are compatible with the fingerprint recognition system 38 having chemical analysis capabilities.

For example, a user of the mobile device 30 may have a plurality of software applications on his/her smart phone. When the user inputs a fingerprint via the fingerprint recognition system 38, the smart phone may make software application recommendations based on the fingerprint inputted. If the chemical analysis performed identifies the user as a 22-year old, white male who enjoys smoking and eating red meat, the smart phone may recommend a plurality of different things based on such results. For example, a plurality of video games may be recommended or a plurality of books may be recommended or a plurality of restaurants may be recommended, etc. The information/data/recommendations provided may relate to any topic, for example, games, music, social networking, news, weather, sports, maps, navigation search, videos, movies, entertainment, food, drinks, communication, banking, finance, shopping, retail, productivity, travel, and lifestyle or a combination thereof.

The mobile device 30 may further comprise peripheral devices and/or subsystems. Such peripheral devices and/or subsystems may include, for example, a flash memory, a random access memory (RAM), and/or an auxiliary input/output (I/O) subsystem (e.g., a scroll wheel, trackball, joystick, directional-pad, touch-screen or other navigational component). The peripheral devices and/or subsystems may also include a serial port (e.g., a Universal Serial Bus, or "USB" port), an input device, a speaker, and/or a microphone. A mobile device short-range communications subsystem and/or another device subsystem designated generally by reference may also be provided. The short-range communication subsystem may comprise, for example, an infrared transceiver, wireless bus protocol system, such as Bluetooth™, and/or other means of local wireless communications.

In other words, based on the inputted fingerprint and the chemical analysis of such fingerprint to determine a plurality of characteristics of the user, a plurality of different, for example, recommendations may be provided instantly, in real-time to the user. Thus, there is a direct correlation or direct relationship between the chemical analysis of the fingerprint (e.g., the detected molecular compounds, etc.) and the feedback (e.g., responses, results, recommendations, etc.) provided to the user.

It is noted that even though an electronic book and a mobile device have been described herein (see FIGS. 1 and 2), that any type of electronic device, as defined herein, may be equipped with a fingerprint recognition, collection, and analysis system having chemical analysis capabilities. All these electronic devices may include some type of energizing mechanism to provide power to the fingerprint system. For instance, the energizing mechanism may be a battery, a solar panel, or any other type of mechanism for providing power to the fingerprint analysis device. The energizing mechanism may be a wired mechanism or a wireless mechanism. The energizing mechanism may be located in the vicinity of the fingerprint analysis device or may be located within a distant predetermined radius of the fingerprint analysis device.

For instance, in another non-limiting example, a TV remote control may include a fingerprint recognition system having chemical analysis capabilities. The user may input a fingerprint via the remote control. The remote control may analyze the fingerprint via a chemical analysis processor. The remote control may transmit information/data/analysis results to the TV. The TV may display (e.g., on a small portion of the screen or provide a new screen) a list of recommendations related to movies or TV shows the user may be interested in based on the chemical composition of the fingerprint received. It is known that TV stations use Nielsen ratings to determine audience size per age groups (audience measurement information). As such, a direct fingerprint input onto a remote control device may aid TV stations in recruiting new audience members to view their programming based on the chemical analysis of the fingerprints received or inputted.

For instance, in another non-limiting example, a fingerprint scanner may be integrally constructed with a steering wheel to determine the chemical characteristics of the driver in order to, for example, reduce the speed of the vehicle if the driver is angry or provide a food recommendation based on the location of the driver. Thus, location-specific recommendations or results or feedback may be provided based on chemical analysis characteristics of drivers of vehicles.

Figure 3A:
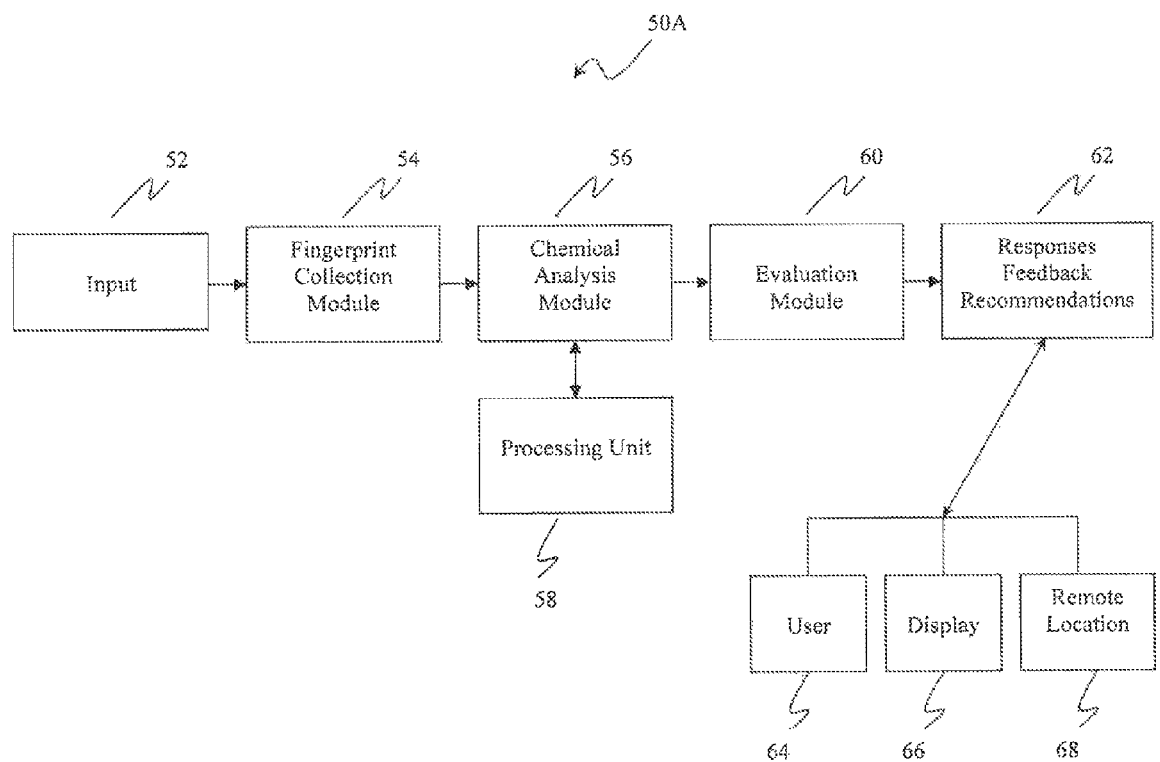
FIG. 3A is a system block diagram of a fingerprint recognition and analysis system for performing chemical analysis of a fingerprint and providing responses, feedback, recommendations to a user, a display unit or an external, remote location, in accordance with the present disclosure.

With reference to FIG. 3A, there is presented a system block diagram of a fingerprint recognition and analysis system for performing chemical analysis of a fingerprint and providing responses, feedback, recommendations to a user, a display unit or an external, remote location, in accordance with the present disclosure.

Figure 3B:
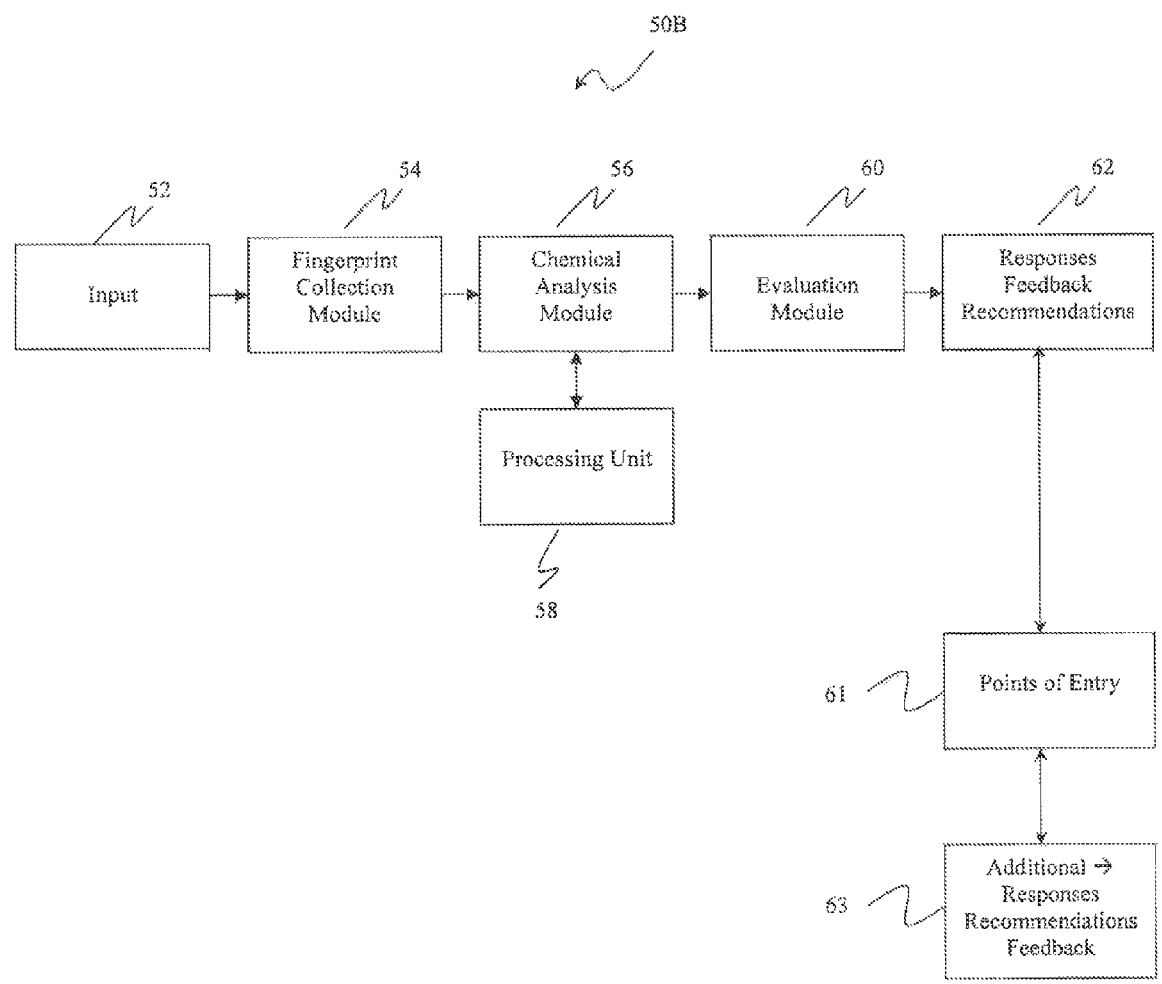
FIG. 3B is a system block diagram of a fingerprint recognition and analysis system for performing chemical analysis of a fingerprint and providing responses, feedback, recommendations to one or more points of entry, in accordance with the present disclosure.

With reference to FIG. 3B, there is presented a system block diagram of a fingerprint recognition and analysis system for performing chemical analysis of a fingerprint and providing responses, feedback, recommendations to one or more points of entry, in accordance with the present disclosure.

Figure 3C:
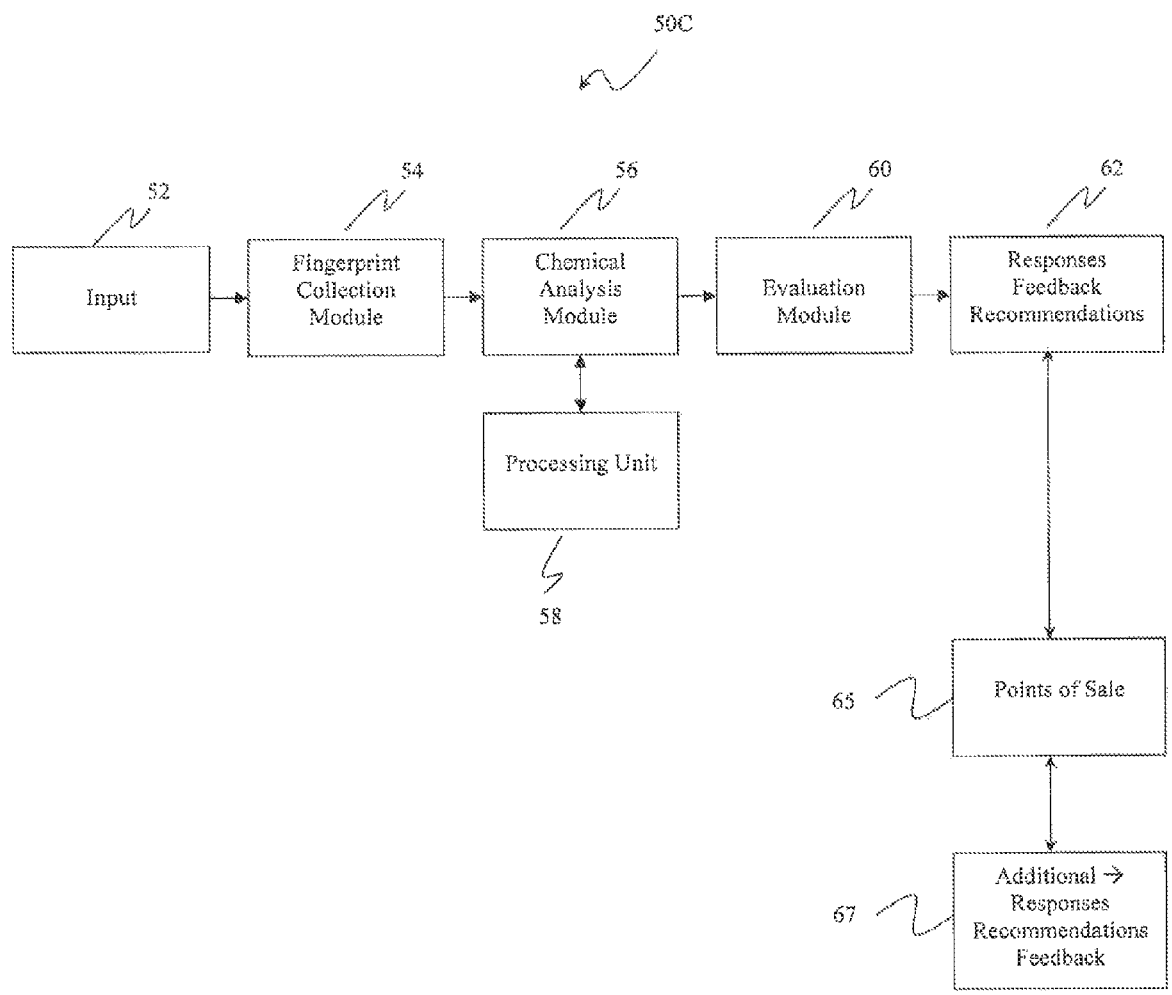
FIG. 3C is a system block diagram of a fingerprint recognition and analysis system for performing chemical analysis of a fingerprint and providing responses, feedback, recommendations to one or more points of sale, in accordance with the present disclosure.

With reference to FIG. 3C, there is presented a system block diagram of a fingerprint recognition and analysis system for performing chemical analysis of a fingerprint and providing responses, feedback, recommendations to one or more points of sale, in accordance with the present disclosure.

System 50A illustrates an input 52 provided to a fingerprint collection module 54. The fingerprint collection module 54 provides the received one or more fingerprints to a chemical analysis module 56, which operates in cooperation with a processing unit 58. Once the received fingerprints or input 52 is processed and chemically analyzed by the chemical analysis module 56, the results are provided to an evaluation module 60, which evaluates the chemical results and provides a recommendation(s) 62. The recommendation(s) 62 may be provided directly to a user 64 (e.g., audible format or text message or images or video) and/or displayed on a display screen 66 (e.g., on an electronic book) and/or may be provided to a remote location 68.

The recommendations 62 may include a plurality of messages based on gender, age, race, dietary information, lifestyle information or a combination thereof determined by the chemical analysis of the fingerprint. For example, a first message may be conveyed to a black, 18-year old male and a second message may be conveyed to a black, 65-year old male. A different message may be conveyed to a 21-year old, white, female vegetarian than a 21-year old, white, female meat-eater. A database (remote or local) may provide for hundreds, if not thousands of messages or recommendations 62, pertaining to myriad combinations of potential fingerprint inputs. Additionally, the fingerprint recognition devices 18, 38 may be programmed (e.g., via software or code) to select a predetermined number of characteristics to analyze to convey a message or recommendation 62 (see FIGS. 10A and 10B).

Any number of characteristics may be derived from the chemical analysis of the input 52. For example, 3 total characteristics may be used, 5 total characteristics may be use or 10 total characteristics may be used (see FIGS. 10A and 10B). One skilled in the art may contemplate using anywhere from 1 characteristic to hundreds, if not thousands, of characteristics (attributes, aspects, features, qualities, traits) to take into consideration before outputting a message or recommendation based on a fingerprint or input 52. A number of different molecules or molecular organic compounds may be analyzed or taken into consideration for assembling or putting together or capturing or collecting one or more responses or recommendations or results.

A transceiver (not shown) may be located about or on or within the fingerprint recognition systems 18, 38 having chemical analysis capabilities or may be located in a remote location with respect to the fingerprint recognition systems 18, 38. The transceiver may be used to receive one or more updated sounds or text, or images or video or information from an external source and to transmit feedback information to the external source. The information may be transmitted or received either in a wired configuration or in a wireless configuration. The transceiver may receive a plurality of different information/data from the external source. The information may be related to updated messages or recommendations 62 to convey to input 52. The information may be transmitted automatically in predetermined time intervals (e.g., daily, weekly, monthly, etc.) or may be transmitted based on demand (or a prompt) from a retail store. The external source may be a computer or electronic device that is continuously updated with messages or recommendations 62 by the manufacturers or sellers or producers of the product/item or display or poster or publication. The external source may be prompted to transmit the updated or new information/messages or may do so in an automatic manner.

Additionally, based on the information received, the information may be recorded and categorized into historical or statistical data in order to allow the manipulators (e.g., advertisers or marketers or sellers or producers or manufacturers, etc.) of the external source to determine which messages or recommendations 62 to send to which locale based on the feedback information. For example, a store in one location may have more white male clientele between the ages of 21-45, whereas a store in another locale may have more white female clientele between the ages of 40-65. As a result, the external source may be calibrated to send more direct targeted output based on such historical or statistical determinations. Once again, a determination is made as to what the characteristics of the subject are. Such characteristics may include at least age, gender, race, dietary information, and/or lifestyle information, or a combination thereof, and targeted messages/output/outcomes (e.g., recommendations, feedback, responses, results, etc.) based on such collected data may be conveyed substantially instantaneously, in real-time.

The system block diagram 50B is similar to the system block diagram 50A of FIG. 3A. Therefore, similar elements to FIG. 3A will not be described in detail. In contrast to FIG. 3A, FIG. 3B includes a points-of-entry module 61 for providing additional recommendations 63. Referring to FIG. 3B, a point-of-entry may be any physical or virtual environment. For example, the point-of-entry (POE) may be a retail store, such as Best Buy™. When a user enters Best Buy™, he/she may approach a kiosk in operative communication with or associated with a fingerprint system having chemical analysis capabilities. The user may input one or more fingerprints, the fingerprint system analyzes the fingerprint(s), derives a number of characteristics based on the chemical signature or blueprint of the fingerprint(s), and provides the user with, for instance, a plurality of recommendations. In an example embodiment, the fingerprint system may determine that the user is a 35-year old, male, of Caucasian descent, who eats anything, etc. The kiosk may include a display means for displaying the top 3 recommended High Definition Light Emitting Diode Televisions in the store, as well as top 3 movies for a person with such characteristics, as well as top 3 newly released singles from rock bands for a person with such characteristics. Such information may be considered as additional recommendations 63. Thus, a point-of-entry may create automatic recommendations for an inputted fingerprint. The database including such feedback information will be described in detail with reference to FIG. 4.

Moreover, in yet another non-limiting example, a POE location may be a museum or art exhibit. For example, most attendees at an art exhibit walk around and preview the artwork. Adjacent each artwork there is usually placed a placard indicating the name of the artist, the name of the artwork, the year it was completed, a short description of the artwork, etc. In accordance with the present disclosure, it is contemplated that fingerprint systems having chemical analysis capabilities may be positioned next to each artwork in an exhibit or museum or similar establishment or at the entrance of the museum or at the entrance of each exhibit. When a patron enters a fingerprint via the fingerprint system(s) having chemical analysis capabilities, he/she may be provided with (e.g., via cell phone or on a common display screen) a recommendation of other artwork he/she may be interested in seeing based on the chemical composition of his/her fingerprints.

Additionally, for example, if a patron enters the Metropolitan Museum of Art in New York City, the patron may approach a fingerprint analysis kiosk located in the main lobby. Since the Metropolitan Museum of Art is a huge museum housing thousands upon thousands of items, it may easily take days to discover such items. However, the chemical analysis of the inputted fingerprint allows the kiosk to present recommendations to the patron, such as, specific exhibits or artworks that the patron would probably prefer or probably have time to see (e.g., in a 3-hour period) based on the chemical analysis of the fingerprint. Therefore, the patron need not aimlessly walk around the museum searching for desired exhibits. The patron may be directed to the artwork or exhibits that have the highest probability of being liked by the patron. For example, an 18-year old male may be directed to the "Arms and Armor" section of the museum displaying armor, firearms, and swords from Europe and Japan, whereas a 65-year old female may be directed to the "Greek and Roman Art" section of the museum displaying jewelry, glass, gems, statues and sarcophagus.

Of course, one skilled in the art may contemplate a myriad of different messages or recommendations that may be displayed or emitted or transmitted or conveyed to a man or a woman. One skilled in the art may contemplate a myriad of different messages or recommendations to be displayed or emitted or transmitted or conveyed based on gender, race, age or other preferences/characteristics or a combinations thereof. A plurality of different messages or recommendations or information may be envisioned by advertising and/or marketing companies/entities that pertain to any cause, economic or non-economic to influence the person who inputted the fingerprint.

The system block diagram 50C is similar to the system block diagrams 50A and 50B of FIGS. 3A and 3B. Therefore, similar elements to FIGS. 3A and 3B will not be described in detail. In contrast to FIGS. 3A and 3B, FIG. 3C includes a points-of-sale module 65 for providing additional recommendations 67. Referring to FIG. 3C, the point-of-sale (POS) may be any physical or virtual environment. For example, the point-of-sale may be a retail store, such as Best Buy™. When a customer approaches a retail counter to purchase an item at Best Buy™, the customer may input a fingerprint at the point-of-sale location, which is in operative communication with or associated with a fingerprint system having chemical analysis capabilities. As the item or items purchased by the consumer are scanned by the store clerk, the fingerprint system may inform the consumer of other items he/she may be interested within the store for current or future purchase based on the chemical characteristics obtained or derived from the fingerprint. Such information may be considered as additional information 67. Thus, a point-of-sale may create automatic recommendations for an inputted fingerprint. The database including such feedback information will be described in detail with reference to FIG. 4.

Figure 4:
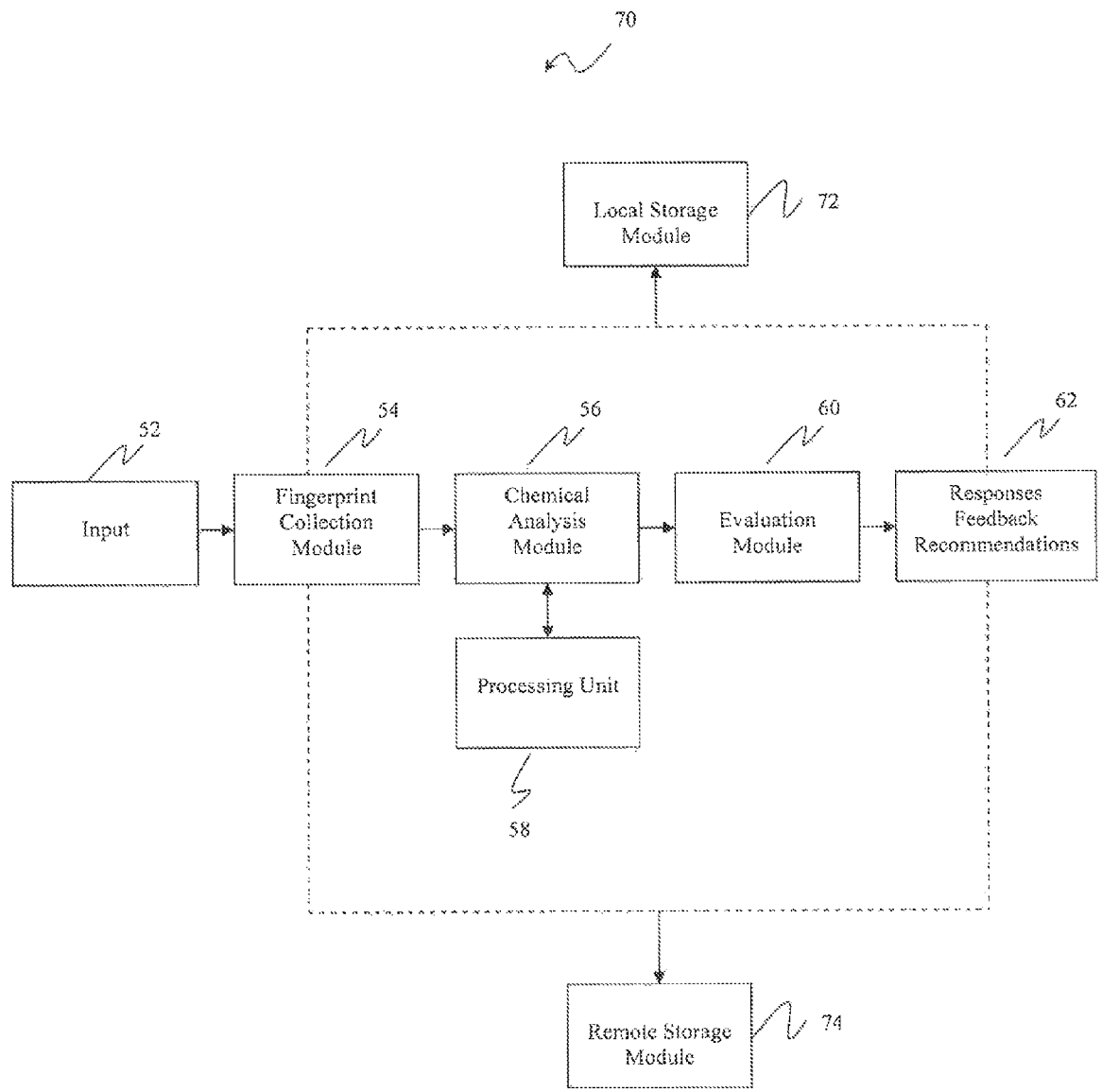
FIG. 4 is a system block diagram of a fingerprint recognition and analysis system for performing chemical analysis of a fingerprint having local and/or remote storage modules, in accordance with the present disclosure.

With reference to FIG. 4, there is presented a system block diagram of a fingerprint recognition and analysis system for performing chemical analysis of a fingerprint having local and/or remote storage modules, in accordance with the present disclosure.

The system block diagram 70 is similar to the system block diagrams 50A, 50B, 50C of FIGS. 3A, 3B, 3C. Therefore, similar elements to FIGS. 3A, 3B, and 3C will not be described in detail. In contrast to FIGS. 3A, 3B, 3C, FIG. 4 includes a local storage module 72 and/or a remote storage module 74.

Storage modules 72, 74 (or memory elements) may be any type of data storage systems, as defined herein. Storage modules 72, 74 may be storage units or memory units. The storage modules 72, 74 may be one or more databases. The storage modules 72, 74 may include a plurality of records. The storage modules 72, 74 may be centralized (as in a fingerprint repository) or distributed (as in a plurality of fingerprint scanners). The records may be stored in the form of a table, list, or other data structure (or combination of data structures) known to those of skill in the art. Each of the records may include an identifier field, which stores a unique identifier associated with chemical characteristic combinations obtained by the fingerprint system having chemical analysis capabilities. Thus, each of the records in the storage modules 72, 74 may be associated with a message directly associated with or correlated to one or more characteristics of the input fingerprint.

Figure 5:
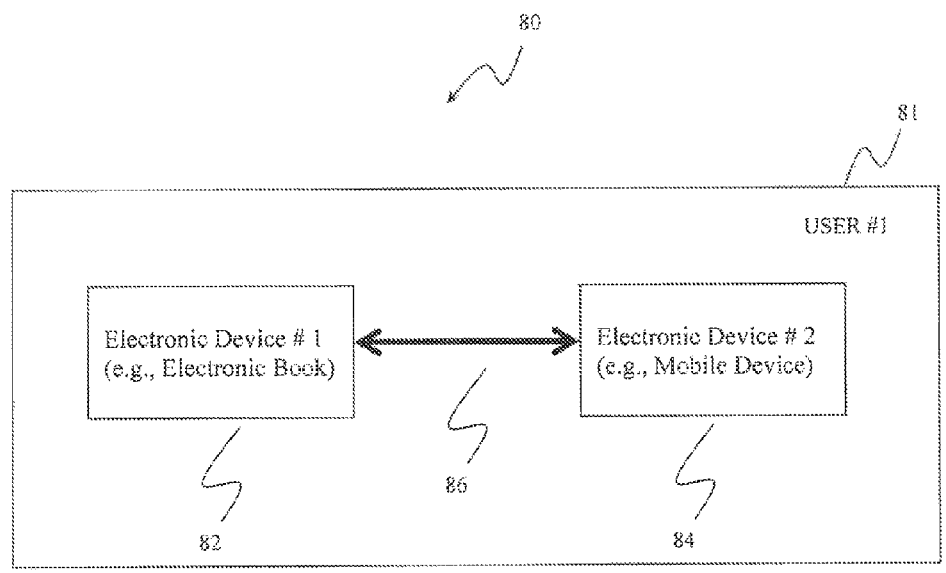
FIG. 5 is a block diagram depicting the transfer of chemical analysis information, processed by a processor, between electronic devices operated by a common user, in accordance with the present disclosure.

With reference to FIG. 5, there is presented a block diagram depicting the transfer of chemical analysis information, processed by a processor, between electronic devices operated by a common user, in accordance with the present disclosure.

Block diagram 80 illustrates communication 86 between a first electronic device 82 and a second electronic device 84. Both electronic devices 82, 84 are owned or operated or used by a common user 81. For example, the first electronic device 82 may be an electronic book. As the user is reading a novel with the first electronic device, a fingerprint input of the user may inform the user of another 5 novels that the user would most likely enjoy based on the inputted fingerprint (and subsequent chemical analysis of the fingerprint). Furthermore, the second electronic device 84 may be a mobile device, such as an iPhone®. The user may enjoy a certain game. As the user inputs a fingerprint and then finishes playing the game, the iPhone® may display visual images of top ten games for such a user. Such recommended information may be shared between the first electronic device 82 and the second electronic device 84 via communication link 86. Thus, a user having several electronic devices is permitted to share such recommended information between the electronic devices and store (local or remote storage) such information on any of the electronic devices commonly owned or operated or within the same household.

Figure 6:
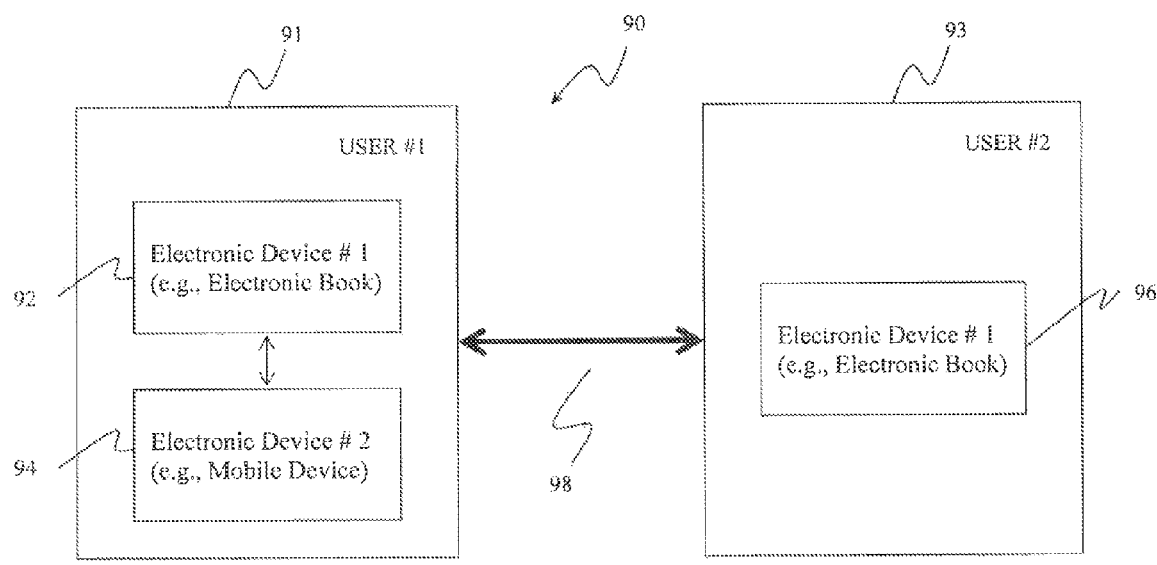
FIG. 6 is a block diagram depicting the transfer of chemical analysis information, processed by a processor, between electronic devices operated by different users, illustrating the sharing of such information between a plurality of users, in accordance with the present disclosure.

With reference to FIG. 6, there is presented a block diagram depicting the transfer of chemical analysis information, processed by a processor, between electronic devices operated by different users, illustrating the sharing of such information between a plurality of users, in accordance with the present disclosure.

Block diagram 90 illustrates a first user 91 having commonly owned or operated electronic devices 92, 94. Each of the electronic devices 92, 94 include a fingerprint system having chemical analysis capabilities. Additionally, block diagram 90 illustrates a second user 93 having an electronic device 96. The electronic device 96 includes a fingerprint system having chemical analysis capabilities. The electronic devices 92, 94 of the first user 91 are permitted to communicate with the electronic device 96 of the second user 93 via communications link 98. Thus, a plurality of different users may share or exchange recommended information received from their respective electronic devices. The first user 91 may send a list of his recommended top 10 books to read to the second user 93, and the second user 93 may send a list of her recommended top 10 books to the first user 91. As such, the first and second users 91, 93 may, for example, talk about the books on the recommended lists.

Of course, one skilled in the art may contemplate exchanging any type of information/data received via the chemical analysis of his/her fingerprint to a number of different users of various different electronic devices. Thus, an electronic book may communicate its information to any other electronic device(s) of the same user (as described with reference to FIG. 5) or of different users of electronic devices (as described with reference to FIG. 6).

Figure 7:
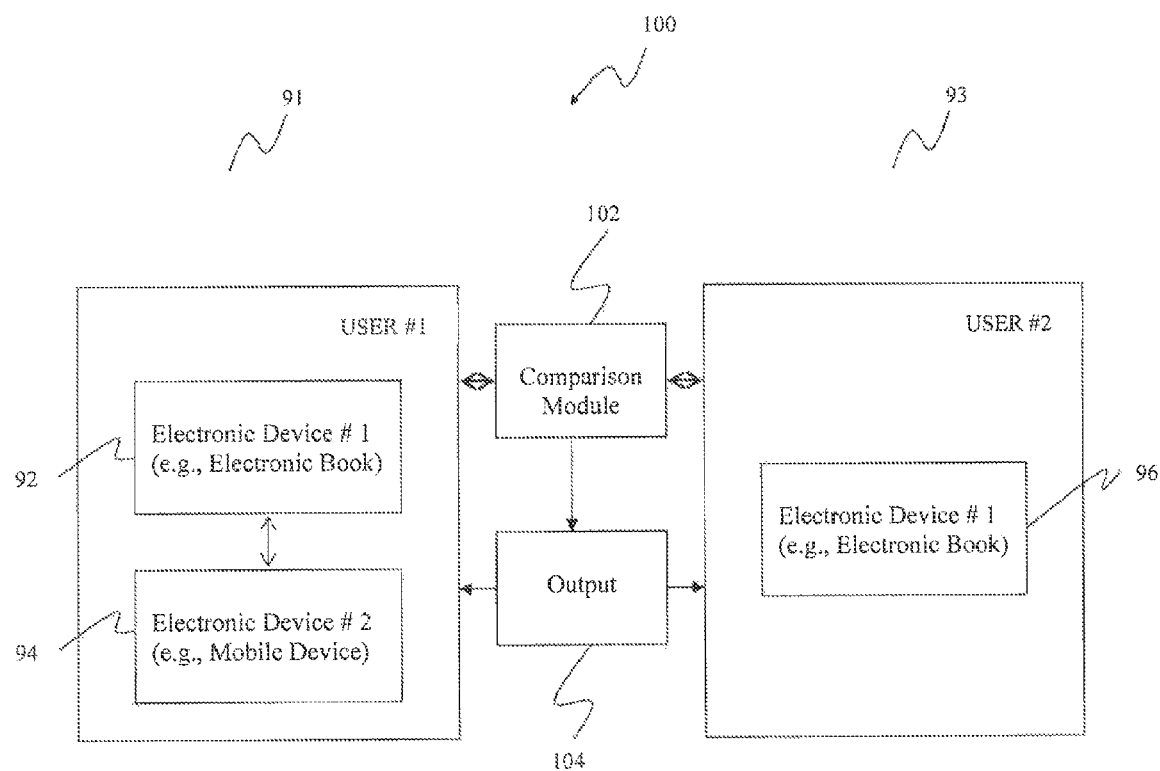
FIG. 7 is a block diagram depicting the transfer of chemical analysis information, processed by a processor, between electronic devices, where a comparison module compares responses of the electronic devices of different users for determining at least common preferences, in accordance with the present disclosure.

With reference to FIG. 7, there is presented a block diagram depicting the transfer of chemical analysis information, processed by a processor, between electronic devices, where a comparison module compares responses of the electronic devices of different users for determining at least common preferences, in accordance with the present disclosure.

Block diagram 100 includes a first user 91 having commonly owned or operated electronic devices 92, 94. Each of the electronic devices 92, 94 include a fingerprint system having chemical analysis capabilities. Additionally, block diagram 90 illustrates a second user 93 having an electronic device 96. The electronic device 96 includes a fingerprint system having chemical analysis capabilities. The electronic devices 92, 94 of the first user 91 are permitted to communicate with the electronic device 96 of the second user 93. Thus, a plurality of different users may share or exchange recommended information received from their respective electronic devices. Additionally, expanding the concepts described in FIG. 6, a comparison module 102 may be provided. The comparison module 102 may compare the recommended results of the first user 91 and the second user 93 and send such output 104 to the users 91, 93 or may send such output 104 to a remote location 68 (see FIG. 3A) or to storage modules 72, 74 (see FIG. 4).

Figure 8:
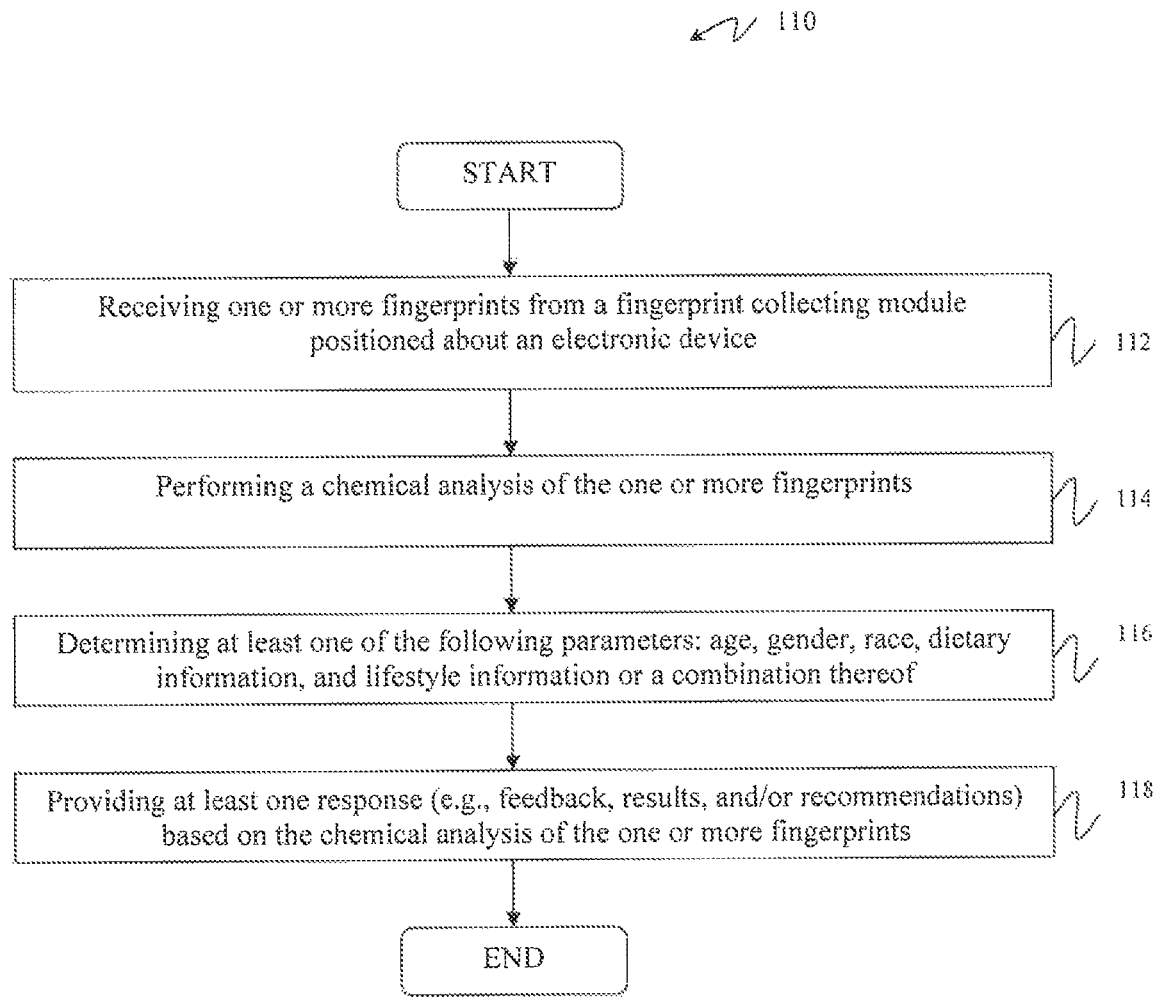
FIG. 8 is a flowchart illustrating performing chemical analysis via at least one electronic device and providing at least one response based on the chemical analysis, in accordance with the present disclosure.

With reference to FIG. 8, there is presented a flowchart illustrating performing chemical analysis via at least one electronic device and providing at least one response based on the chemical analysis, in accordance with the present disclosure.

The flowchart 110 includes the following steps. In step 112, one or more fingerprints are received from a fingerprint collecting module positioned on or about an electronic device. In step 114, a chemical analysis is performed on the one or more fingerprints collected by the fingerprint collection module. In step 116, at least one of the following parameters is determined by a chemical analysis module: age, gender, race, dietary information and/or lifestyle information or a combination thereof. In step 118, at least one response (e.g., feedback, results, recommendations, etc.) is provided based on the chemical analysis of the one or more fingerprints. The process then ends for the first cycle or first iteration. However, the process may be a continuous iterative process. In other words, the steps of the process may repeat for a number cycles or iterations, where at least the scanning, transmitting, receiving, and analyzing steps are constantly repeated.

Figure 9:
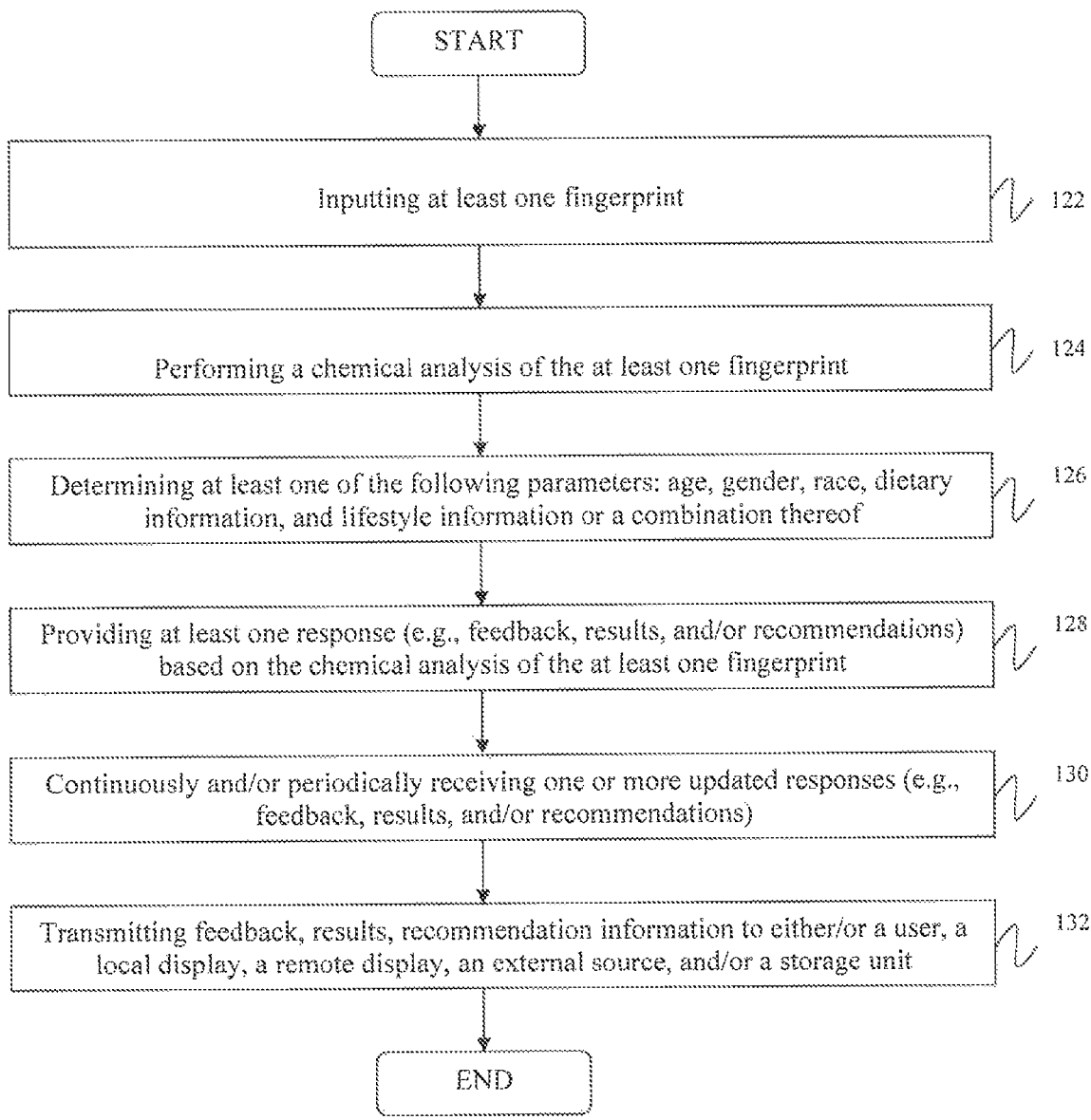
FIG. 9 is a flowchart illustrating performing chemical analysis via at least one electronic device and providing at least one updated response continuously and/or periodically, in accordance with the present disclosure.

With reference to FIG. 9, there is presented a flowchart illustrating performing chemical analysis via at least one electronic device and providing at least one updated response continuously and/or periodically, in accordance with the present disclosure.

The flowchart 120 includes the following steps. In step 122, at least one fingerprint is inputted. In step 124, a chemical analysis of the at least one fingerprint is performed. In step 126, at least one of the following parameters is determined by a chemical analysis module: age, gender, race, dietary information and/or lifestyle information or a combination thereof. In step 128, at least one response (e.g., feedback, results, recommendations, etc.) is provided based on the chemical analysis of the one or more fingerprints. In step 130, one or more updated responses are continuously or periodically received (e.g., from an external source). In step 132, feedback, results, and/or recommendation information is transmitted back to either/or a user, a local display, a remote display, an external source, and/or a storage unit. The process then ends for the first cycle or first iteration. However, the process may be a continuous iterative process. In other words, the steps of the process may repeat for a number cycles or iterations, where at least the scanning, transmitting, receiving, and analyzing steps are constantly repeated.

Figure 10A:
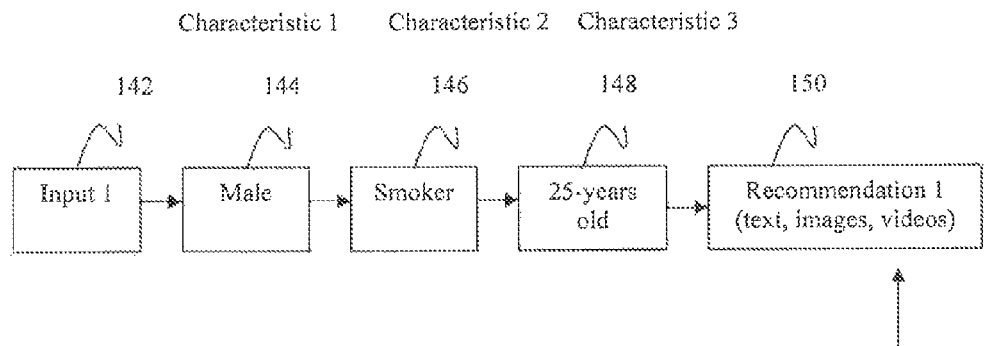
FIGS. 10A and 10B, are block diagrams illustrating different output recommendations (or responses or feedback or results) based on different characteristics analyzed by the fingerprint recognition system, in accordance with the present disclosure.
Figure 10B:
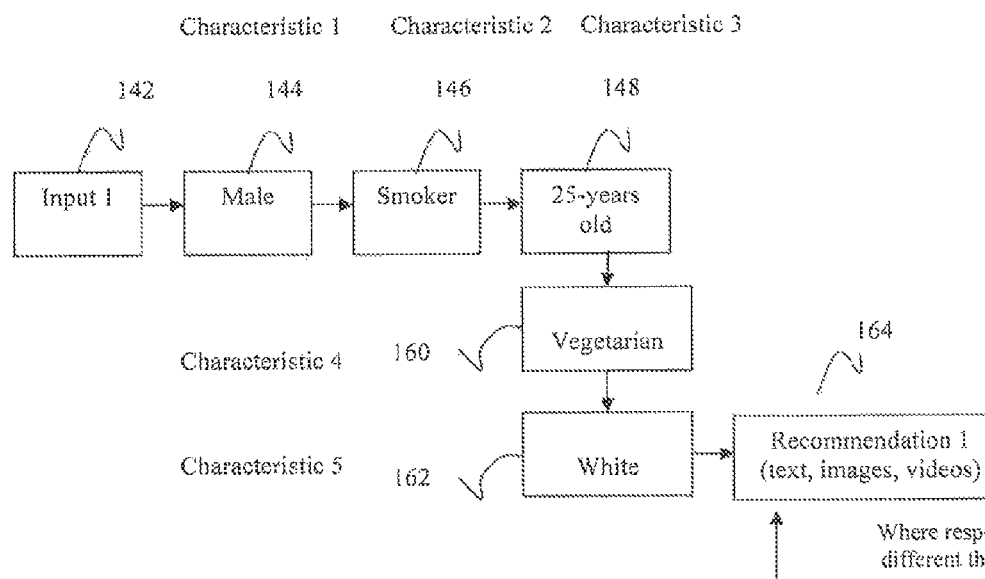

With reference to FIGS. 10A and 10B, there is presented block diagrams illustrating different output recommendations (or responses or feedback or results) based on different characteristics analyzed by the fingerprint recognition system, in accordance with the present disclosure.

The first sequence 140A of FIG. 10A includes a first input 142. The first input 142 is a fingerprint voluntarily inputted by a consumer (or user or owner of an electronic device) to activate the fingerprint analysis devices, as described herein. In this example, the sensing mechanism(s) of the fingerprint analysis devices may be programmed to detect 3 main characteristics of the consumer based on the inputted fingerprint. For example, first characteristic 144 may relate to the gender (e.g., male), the second characteristic 146 may relate to a lifestyle choice (e.g., smoker), and the third characteristic 148 may relate to age (e.g., 25 years old). Based on those 3 detected characteristics, the fingerprint analysis device may output a first message 150 (e.g., recommendation), which is at least text or images or videos or audible sounds or a combination thereof.

The second sequence 140B of FIG. 10B includes the first input 142. The first input 142 is a fingerprint voluntarily inputted by a consumer to activate the fingerprint analysis devices, as described herein. In this example, the sensing mechanism of the fingerprint analysis devices may be programmed to detect 5 main characteristics of the consumer (or user or owner of an electronic device) based on the inputted fingerprint. For example, first characteristic 144 may relate to the gender (e.g., male), the second characteristic 146 may relate to a lifestyle choice (e.g., smoker), the third characteristic 148 may relate to age (e.g., 25 years old), the fourth characteristic 160 may relate to an additional lifestyle choice (e.g., vegetarian), and the fifth characteristic 162 may relate to race (e.g., white). Based on those 5 detected characteristics, the fingerprint analysis device may output a second message 164 (e.g., recommendation), which is at least text or images or videos or audible sounds or a combination thereof. The second message 164 may be the same or may be different than the first message 150 of FIG. 10A. This determination may be based on the sophistication in the software developed to decide what recommendations or responses or feedback to output based on the chemical analysis of the fingerprints received.

Figure 11A:
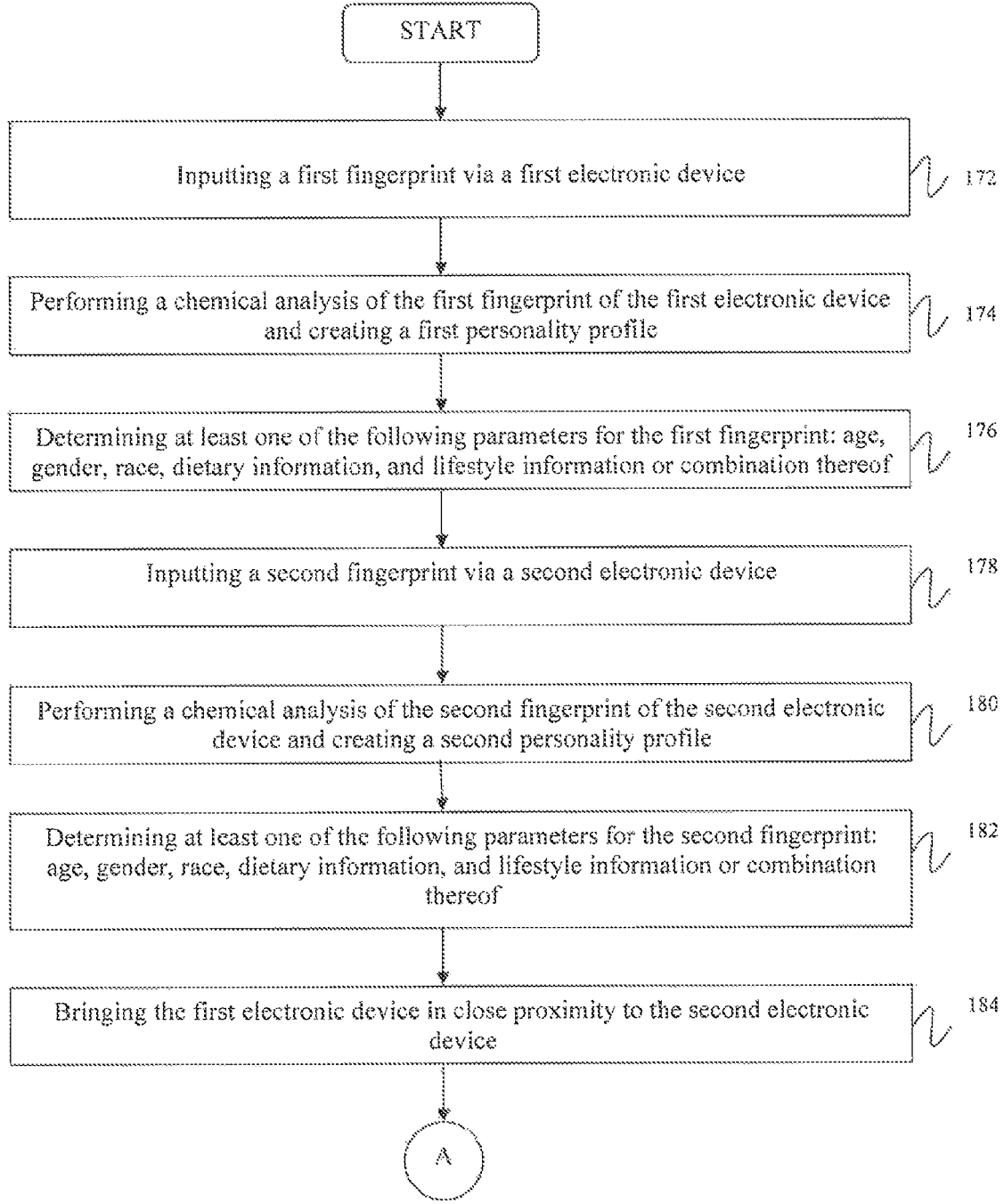
FIGS. 11A-11B illustrate a flowchart for performing chemical analysis on two electronic devices, where the electronic devices are brought into close proximity to exchange fingerprint and chemical profile information for at least compatibility purposes, in accordance with the present disclosure.
Figure 11:
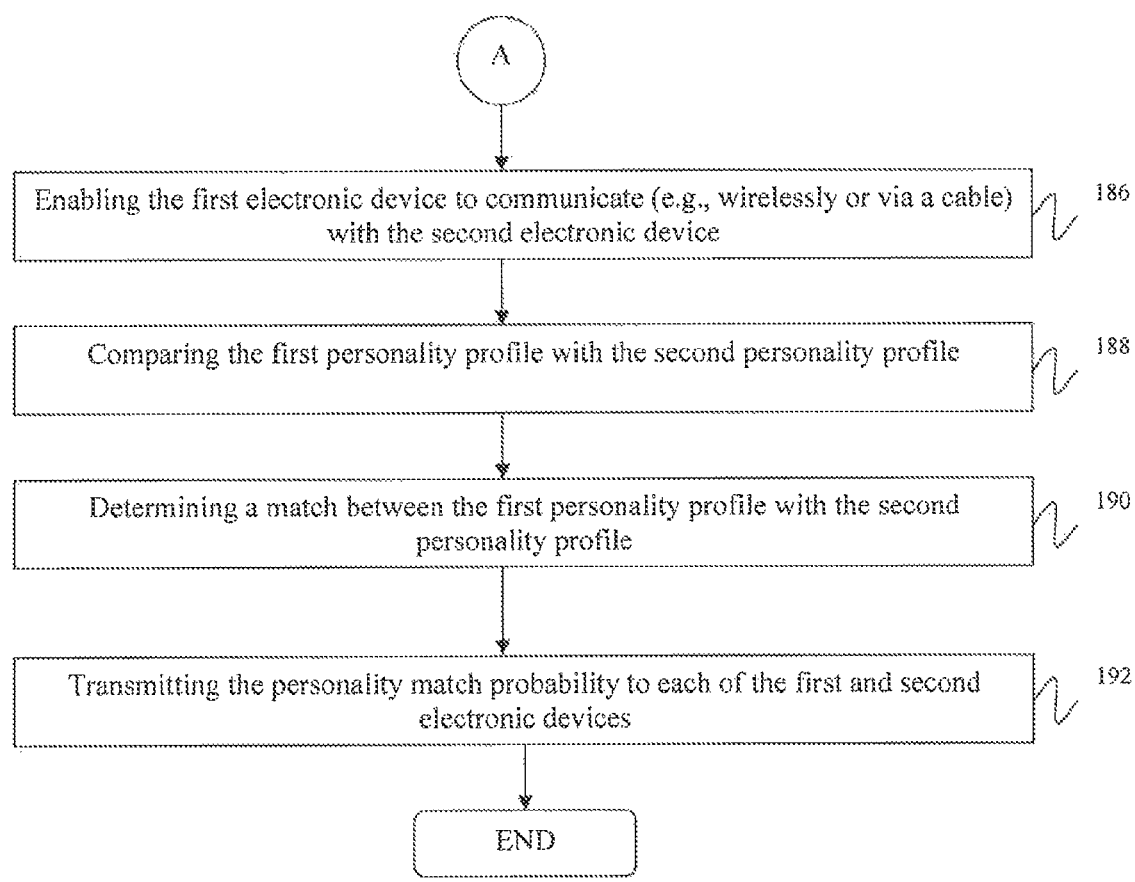

With reference to FIGS. 11A-11B, there is presented a flowchart illustrating performing chemical analysis on two electronic devices, where the electronic devices are brought into close proximity to exchange fingerprint and chemical profile information for at least compatibility purposes, in accordance with the present disclosure.

The flowchart 170 includes the following steps. In step 172, a first fingerprint is inputted via a first electronic device. In step 174, a chemical analysis of the first fingerprint of the first electronic device is performed and a first personality profile is created. In step 176, at least one of the following parameters is determined by a chemical analysis module: age, gender, race, dietary information and/or lifestyle information or a combination thereof. In step 178, a second fingerprint is inputted via a second electronic device. In step 180, a chemical analysis of the second fingerprint of the second electronic device is performed and a second personality profile is created. In step 182, at least one of the following parameters is determined by a chemical analysis module: age, gender, race, dietary information and/or lifestyle information or a combination thereof. In step 184, the first electronic device is brought in close proximity to the second electronic device. In step 186, the first electronic device communicates with the second electronic device. In step 188, the first personality profile is compared to the second personality profile. In step 190, a potential match is determined between the first personality profile and the second personality profile. In step 192, the personality match probability is transmitted to each of the first and second electronic devices. The process then ends for the first cycle or first iteration. However, the process may be a continuous iterative process. In other words, the steps of the process may repeat for a number cycles or iterations, where at least the inputting, scanning, transmitting, receiving, analyzing, enabling, comparing, and matching steps are constantly repeated.

Therefore, in accordance with FIGS. 11A-11B, a dating service may be created based on chemical analysis of fingerprints. A first electronic device (e.g., a smart phone) of a first user may chemically analyze the fingerprint of the first user to create a first personality profile. Similarly, a second electronic device (e.g., a smart phone) of a second user may chemically analyze the fingerprint of the second user to create a second personality profile. The users may exchange such information in order to determine dating compatibility. For example, the users may bump each others smart phones at a party to determine dating compatibility. It is known that there is an iPhone® application called "Bump" that allows people to exchange contact information by literally bumping iPhones together. The comparison module 102 (see FIG. 7) may compare the personality profiles and determine or predict if a love match is a high probability. Of course one skilled in the art may contemplate a plurality of different ways for exchanging any type of information between any type electronic devices, as defined herein. Additionally, if a match is determined, one or more messages may be permitted to be transmitted between the electronic devices. For example, a file transfer or music file or photograph or images or video clips or text or email exchange(s) may take place.

Thus, an electronic device that uses a fingerprint system having chemical analysis capabilities may help find someone who fits a predetermined description or criteria. The electronic devices may continuously emit an automatic and generally continuous signal. The signal may interrogate other electronic devices located within a range of the electronic devices to predict or determine compatibility. Preferably, the compatibility profiles are determined via the chemical analyses of fingerprints. Visual and/or audible alerts may be provided to each party to inform them of a compatibility match or correlation. The parties may be alerted to the presence of compatible types within a predetermine area, along with an indication of a degree of correlation found and whether a selected matching signal's position is masked (described below). The party would have the option of unmasking his/her position to the emitter of a specific signal. It should be possible to see the target party at a safe distance before making further contact. The signals may be transmitted automatically or intermittently. As such, the parties have the option of communicating immediately after, for example, smart phone "bumps" have taken place.

In an alternative embodiment, a "MASK" switch may be incorporated within or about the hardware or the software of the electronic device to allow a party to mask his/her location. Of course, one skilled in the art may contemplate encrypting any analog or digital signals transmitted between electronic devices and/or between electronic devices and networks. The plurality of electronic devices may communicate at least within a local network, within a cellular telephone network, remote networks, satellite networks, Wi-Fi networks, WiMAX networks, ultra-wideband networks, Voice over Internet Protocol (VoIP) networks, etc.

Alternatively, the fingerprint analysis device may convey both audible and non-audible messages. For example, the manufacturer may determine whether audible or non-audible messages are conveyed, separately or simultaneously. However, it is contemplated that a user may be permitted to select either an audible or non-audible message directly from the fingerprint analysis systems presented herein. A separate selection mechanism may be positioned on such fingerprint analysis systems.

Alternatively, a plurality of fingerprint analysis systems may be positioned on or about each electronic device. The fingerprint analysis systems may be positioned anywhere on the electronic devices, even directly on the display screen(s).

Alternatively, an illuminating unit/module/device may be positioned adjacent the fingerprint recognition, collection, and analysis devices to illuminate the area received by the fingerprint scanner (e.g., gel-tape receiving an impression).

The additional light may aid the fingerprint scanner in scanning higher quality fingerprint images.

Alternatively, more than one message or recommendation may be conveyed in response to an inputted fingerprint. For example, the fingerprint analysis devices may be constructed to convey 2 back-to-back messages or recommendations (on different topics of interest) based on the input. The fingerprint analysis devices may convey 3 messages or more. It is contemplated that the fingerprint analysis devices may convey a plurality of different messages or recommendations based on one inputted fingerprint. It is also contemplated that the user may request more than one message or recommendation after voluntarily inputting a fingerprint to the fingerprint analysis devices, as described herein.

Alternatively, it is contemplated that any existing, current or future electronic device may be conveniently transformed by adding a fingerprint analysis device for collecting fingerprints, analyzing the chemical composition of the fingerprints, determining the characteristics of the inputted fingerprints, and outputting targeted messaging (e.g., recommendations, responses, feedback, supplemental information, etc.) based on the fingerprint input.

Alternatively, fingerprint-specific searches may be enabled via Google™ or other search engines (e.g., Bing™). For example, the fingerprint systems described herein may be embedded within or positioned onto a display means (e.g., an LCD PC screen). The user may go to Google™ and type in a key term. The user may contact the LCD screen of the PC to activate the chemical analysis of the fingerprint. The chemical analysis results may trigger a new Google™ search related to preferences obtained from the chemical analysis of the inputted fingerprint. Thus, Internet searching or browsing may be automatically performed by touching or contacting a fingerprint system as described herein. The chemical analysis of the fingerprint may influence the search results (targeted searching). In other words, a different set of search results may be provided by a search engine to a 21-year-old males versus a 75-year-old male, based on the chemical analysis of their respective fingerprints. Thus, the exemplary embodiments of the present disclosure enable touch-specific searching, touch-specific results, touch-specific outcomes and/or outputs and/or trails.

Alternatively, law enforcement agents may have access to a database where such fingerprint images are stored in order to compare such fingerprint images to pre-stored or prerecorded fingerprint images for the detection of persons of interest (e.g., criminals, fugitives, etc.). Such an alternative embodiment has been contemplated in an application filed on Jun. 8, 2010, having Ser. No. 12/802,491 entitled "System and Method for Fingerprint Recognition and Collection at Points-of-Sale and Points-of-Entry," filed by the current Applicant, the contents of which are incorporated by reference herein in their entirety.

Alternatively, the exemplary embodiments of the present disclosure may be combined with methods and systems for instant fingerprint recognition, reception, collection, transmission, storage, and/or analysis resulting in targeted audible and/or non-audible output. Such an alternative embodiment has been contemplated in an application filed on Jul. 27, 2010, having Ser. No. 12/804,705 entitled "System and Method for Instantaneous Fingerprint Recognition and Analysis Resulting in Targeted Output," filed by the current Applicant, the contents of which are incorporated by reference herein in their entirety.

Concerning privacy issues, it is believed that under the $4^{th}$ Amendment that privacy issues would be inapplicable in such a scenario presented in the exemplary embodiments of the present disclosure. The $4^{th}$ Amendment (Amendment IV) to the United States Constitution is the part of the Bill of Rights which guards against unreasonable searches and seizures. The question is whether collecting voluntary fingerprints from individuals would violate the $4^{th}$ Amendment. In order to answer this question, one would pose the following inquiry: Does one have a reasonable expectation of privacy in their fingerprints? The criteria for determining if one has a reasonable expectation of privacy are as follows: 1) general legal principles; 2) the vantage point from which the surveillance is carried out; 3) the degree of privacy afforded by certain buildings and/or places; and 4) the sophistication and invasiveness of the surveillance technology employed. In the exemplary embodiments of the present disclosure, one does not have a degree of privacy in their fingerprints. By voluntarily touching things/items/products and/or electronic devices in general, one gives up their privacy to their fingerprints. Thus, the systems and methods presented herein would be compatible and in line with important legal principles and would not violate the U.S. Constitution. It is anticipated that in the exemplary embodiments of the present disclosure that the individuals voluntarily provide their fingerprint to aid the fingerprint analysis device in determining which recommendations to convey.

Additionally, when implemented via executable instructions, various elements of the present disclosure are in essence the code defining the operations of such various elements. The executable instructions or code may be obtained from a readable medium (e.g., a hard drive media, optical media, EPROM, EEPROM, tape media, cartridge media, flash memory, ROM, memory stick, and/or the like) or communicated via a data signal from a communication medium (e.g., the Internet). In fact, readable media may include any medium that may store or transfer information. Additionally, "code" as used herein, or "program" as used herein, may be any plurality of binary values or any executable, interpreted or compiled code which may be used by a computer or execution device to perform a task. This code or program may be written in any one of several known computer languages. A "computer," as used herein, may mean any device which stores, processes, routes, manipulates, or performs like operation on data. A "computer" may be incorporated within one or more fingerprint recognition and collection systems or servers to operate one or more processors to run the fingerprint recognition algorithms. The term "computer" may be equivalent to or interchangeable with the term "electronic device."

Moreover, computer-executable instructions include, for example, instructions and data which cause a general purpose computer, special purpose computer, or special purpose processing device to perform a certain function or group of functions. Computer-executable instructions also include program modules that may be executed by computers in stand-alone or network environments. Generally, program modules include routines, programs, objects, components, and data structures, etc. that perform particular tasks or implement particular abstract data types.

A service provider may be any entity that develops, offers, controls, manages, owns, alters and/or sells software and/or hardware products and/or items or products or publications. A service provider may be any entity that performs one or more tasks on one or more pre-existing fingerprint systems, which may or may not be controlled or owned by the service provider. For example, the entity may offer a service with an existing software package and/or with any type of existing Internet-based service through the Internet. In other words, a service provider need not own or provide the fingerprint systems. The fingerprint systems may be owned or provided by any third party not related or associated with the service provider. In the present disclosure, it may be contemplated that the entity (such as a service provider) may offer any type of service and/or product to optimize pre-existing, pre-owned fingerprint systems by referring potential customers to an Internet website or a store that may or may not be associated with fingerprint system-related services and/or products. The term "entity" may refer to anything that may exist as a discrete and/or distinct unit that owns, operates, manages, and/or controls one or more of a plurality of machines (such as fingerprint systems). For example, the term "entity" may include the term "company." Thus, the exemplary embodiments of the present disclosure also cover service providers of fingerprint methods and systems. In other words, various service providers may use the fingerprint systems of the present disclosure, which include chemical analysis capabilities in order to act as third-party members of a network.

It will be understood that there are to be no limitations as to the dimensions and shape of the fingerprint systems, including the storage compartment, or the materials from which the fingerprint systems are manufactured or the electronics that may be used to run such a fingerprint system and/or fingerprint scanners (e.g., one or more biomaterials and/or biochips and/or gel biochips and/or biosensors and/or bio-electronic sensors and/or microprocessors).

The foregoing examples have been provided merely for the purpose of explanation and are in no way to be construed as limiting of the present method and system disclosed herein. While the present disclosure has been described with reference to various embodiments, it is understood that the words, which have been used herein, are words of description and illustration, rather than words of limitations. Further, although the present disclosure has been described herein with reference to particular means, materials and embodiments, the present disclosure is not intended to be limited to the particulars disclosed herein; rather, the present disclosure extends to all functionally equivalent structures, methods and uses, such as are within the scope of the appended claims. Those skilled in the art, having the benefit of the teachings of this specification, may effect numerous modifications thereto and changes may be made without departing from the scope and spirit of the present disclosure in its aspects.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

Having described the present disclosure above, various modifications of the techniques, procedures, material and equipment will be apparent to those in the art. It is intended that all such variations within the scope and spirit of the appended claims be embraced thereby.

The foregoing examples illustrate various aspects of the present disclosure and practice of the methods of the present disclosure. The examples are not intended to provide an exhaustive description of the many different embodiments of the present disclosure. Thus, although the foregoing present disclosure has been described in some detail by way of illustration and example for purposes of clarity and understanding, those of ordinary skill in the art will realize readily that many changes and modifications may be made thereto without departing form the spirit or scope of the present disclosure.

The invention claimed is:

1. An electronic device comprising:
 a fingerprint collecting module for collecting fingerprint information; and
 a chemical analysis module for performing a chemical analysis of the fingerprint information to create a chemical profile for identifying at least a select number of molecules and/or organic compounds for deriving distinguishing characteristics from the fingerprint information.

2. The electronic device according to claim 1, wherein the chemical analysis is performed on-the-spot, in real-time, and/or substantially instantaneously.

3. The electronic device according to claim 1, further comprising:
 an evaluating module for evaluating the distinguishing characteristics of the fingerprint information to provide at least one response formulated from the distinguishing characteristics derived from the select number of molecules and/or organic compounds.

4. The electronic device according to claim 3, wherein the at least one response includes at least one recommendation based on the chemical profile having the distinguishing characteristics derived from the select number of molecules and/or organic compounds of the fingerprint information.

5. The electronic device according to claim 3, wherein the at least one response is conveyed at least as audible messages, visual messages, text, images, or videos or a combination thereof.

6. The electronic device according to claim 3, wherein the at least one response is at least a message, a recommendation, a result, an outcome, an output, feedback, additional information, supplemental information, educational information, targeted information or advertising information or a combination thereof.

7. The electronic device according to claim 1, wherein the chemical analysis derives at least one or more of the following distinguishing characteristics from the fingerprint information to create the chemical profile: age, gender, race, dietary information, and lifestyle information or a combination thereof.

8. The electronic device according to claim 1, wherein the chemical profile is at least a chemical signature, a chemical blueprint, a chemical photograph, a chemical composition, and/or a chemical snapshot.

9. The electronic device according to claim 1, wherein the distinguishing characteristics are at least attributes, aspects, features, qualities, and/or traits.

10. The electronic device according to claim 1, wherein the distinguishing characteristics are recorded and categorized into historical and/or statistical data.

11. A method of creating a chemical profile, the method comprising:
 providing an electronic device;
 collecting fingerprint information from the electronic device;
 performing a chemical analysis of the fingerprint information to create the chemical profile; and
 identifying at least a select number of molecules and/or organic compounds for deriving distinguishing characteristics from the fingerprint information.

12. The method according to claim 11, wherein the chemical analysis is performed on-the-spot, in real-time, and/or substantially instantaneously.

13. The method according to claim 11, further comprising evaluating the distinguishing characteristics of the fingerprint information to provide at least one response formulated from the distinguishing characteristics derived from the select number of molecules and/or organic compounds.

14. The method according to claim 13, wherein the at least one response includes at least one recommendation based on the chemical profile having the distinguishing characteristics derived from the select number of molecules and/or organic compounds of the fingerprint information.

15. The method according to claim 13, further comprising conveying the at least one response at least as audible messages, visual messages, text, images, or videos or a combination thereof.

16. The method according to claim 13, wherein the at least one response is at least a message, a recommendation, a result, an outcome, an output, feedback, additional information, supplemental information, educational information, targeted information or advertising information or a combination thereof.

17. The method according to claim 11, further comprising deriving at least one or more of the following distinguishing characteristics from the fingerprint information to create the chemical profile: age, gender, race, dietary information, and lifestyle information or a combination thereof.

18. The method according to claim 11, wherein the chemical profile is at least a chemical signature, a chemical blueprint, a chemical photograph, a chemical composition, and/or a chemical snapshot.

19. The method according to claim 11, wherein the distinguishing characteristics are at least attributes, aspects, features, qualities, and/or traits.

20. The method according to claim 11, further comprising recording and categorizing the distinguishing characteristics into historical and/or statistical data.

* * * * *